United States Patent [19]

Sohda et al.

[11] Patent Number: 5,716,944
[45] Date of Patent: Feb. 10, 1998

[54] PHOSPHONIC ACID COMPOUNDS, THEIR PRODUCTION AND USE

[75] Inventors: Takashi Sohda, Takatsuki; Shigehisa Taketomi, Ikeda; Tsuneo Oda, Ibaraki, all of Japan

[73] Assignee: Takeda Chemical Industries, Ltd., Osaka, Japan

[21] Appl. No.: 501,022

[22] PCT Filed: Jul. 3, 1995

[86] PCT No.: PCT/JP95/01328

§ 371 Date: Aug. 11, 1995

§ 102(e) Date: Aug. 11, 1995

[87] PCT Pub. No.: WO96/01267

PCT Pub. Date: Jan. 18, 1996

[30] Foreign Application Priority Data

Jul. 4, 1994 [JP] Japan .................... 6-152482

[51] Int. Cl.$^6$ .................... A01N 57/16; A61K 31/66; C07F 9/44
[52] U.S. Cl. .................... 514/119; 558/83; 558/177; 558/190
[58] Field of Search .................... 558/83, 177, 190; 514/119

[56] References Cited

FOREIGN PATENT DOCUMENTS

| | | |
|---|---|---|
| 0 284 359 | 9/1988 | European Pat. Off. . |
| 0 318 235 | 5/1989 | European Pat. Off. . |
| 0 460 488 | 12/1991 | European Pat. Off. . |
| 0 524 023 | 1/1993 | European Pat. Off. . |
| 0 376 197 | 10/1994 | European Pat. Off. . |
| 0 625 522 | 11/1994 | European Pat. Off. . |
| 5-294960 | 11/1993 | Japan . |

*Primary Examiner*—Johann Richter
*Assistant Examiner*—Jane C. Osweecki
*Attorney, Agent, or Firm*—Foley & Lardner

[57] ABSTRACT

The present invention relates to a compound of the general formula (I):

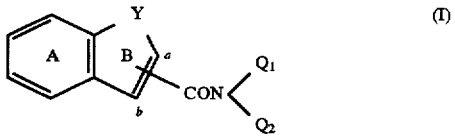

wherein ring A is a benzene ring that may be substituted; Y is a divalent group as a constituent member of ring B forming a 5- to 8-membered ring; $Q_1$ is a group of the formula $—X—P(O)(OR^1)(OR^2)$ wherein X is a bond or a divalent group; $R^1$ and $R^2$, identical or different, are hydrogen or a lower alkyl, or may be combined together to form a ring; $Q_2$ is hydrogen, a hydrocarbon group that may be substituted or a heterocyclic group that may be substituted; and the group of the formula $—CON(Q_1)(Q_2)$ is connected to the a- or b-position carbon atom, or a salt thereof, which is useful as prophylactic and therapeutic agents of various metabolic bone diseases such as osteoporosis.

25 Claims, No Drawings

PHOSPHONIC ACID COMPOUNDS, THEIR PRODUCTION AND USE

This application is a 371 of PCT/JP95/01328 filed Jul. 3, 1995.

1. Technical Field

The invention relates to a phosphonic acid derivative, or salt thereof, that stimulates osteogenesis (bone formation), a method of its production, and a use thereof.

2. Background Art

Osteoporosis is a pathologic state or disease involving some symptoms or risks due to quantitative bone reduction exceeding a certain degree. Major symptoms are spinal kyphosis, and fractures of thoracic vertebrae (dorsolumbar bones), lumber vertebral, femoral necks, distal ends of radius, ribs, proximal ends of humeri, and others. In normal bone tissue, bone destruction occurs constantly, but there is a good balance between bone formation and resorption; osteoblasts and osteoclasts play key roles in bone formation and bone resorption, respectively. Upon deterioration of this balance, bone resorption surpasses bone formation, resulting in onset of osteoporosis associated with quantitative bone reduction. Traditionally, bone resorption inhibitory agents such as estrogens, calcitonin and bisphosphonates have been used to prevent and treat osteoporosis. However, these bone resorption inhibitors fail to have a satisfactory effect in some cases, due to subject limitations or uncertain efficacy. There is therefore need of a new osteogenesis stimulator that positively increases once-decreased bone mass as a prophylactic/therapeutic drug for osteoporosis.

European Patent Publication EP-524023-A1 describes an osteogenesis promoter represented by the formula:

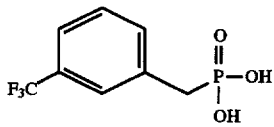

Japanese Patent Unexamined Publication Nos. 232880/1991 and 364179/1992 disclose a 3,4-dihydro-2-benzothiopyran-1-carboxamide derivative and a 1,2,4,5-tetrahydro-3-benzothiepin-2-carboxamide derivative as therapeutic drugs for osteoporosis.

Japanese Patent Unexamined Publication Nos. 230570/1989 and 232864/1991 disclose a 3,4-dihydronaphthalene-2-carboxamide derivative and a 2,3-dihydro-1-benzothiepin-4-carboxamide derivative. However, no carboxamide derivatives are known to have a substitutional phenyl group containing phosphonic acid as an N-substituent.

DISCLOSURE OF INVENTION

The invention provides a phosphonic acid derivative that promotes osteogenesis, a method of its production, and an osteogenesis promoter containing it as an active ingredient.

The present inventors sought to develop a more commonly applicable drug showing direct action on the bone to promote osteogenesis, and found that a phosphonic acid derivative represented by the formula (I) below activates osteoblast function, which is associated directly with osteogenesis promotion, to promote calcification. The inventors made further investigations based on this finding, and developed the present invention.

Accordingly, the present invention relates to:

(1) a compound of the formula (I):

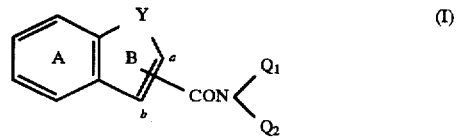

wherein ring A is a benzene ring that may be substituted; Y is a divalent group as a constituent member of ring B forming a 5- to 8-membered ring; $Q_1$ is a group of the formula:

wherein X is a bond or a divalent group; $R^1$ and $R^2$, identical or different, are hydrogen or a lower alkyl group, or may be combined together to form a ring; $Q_2$ is hydrogen, a hydrocarbon group that may be substituted or a heterocyclic group that may be substituted; the group of the formula —CON($Q_1$)($Q_2$) is connected to the a- or b-position carbon atom, or a salt thereof, (2) the compound of term (1), wherein X is a divalent hydrocarbon group and Y is a divalent group as a constituent member of ring B forming a 5- to 7-membered ring, (3) the compound of term (1), wherein $Q_1$ is a group of the formula:

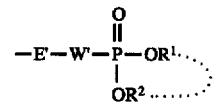

wherein E' is a divalent aromatic hydrocarbon group; W' is a bond or an alkylene group; $R^1$ and $R^2$, identical or different, are hydrogen or a lower alkyl group, or may be combined together to form a ring, (4) the compound of term (3), wherein the divalent aromatic hydrocarbon group is a divalent monocyclic aromatic hydrocarbon group, (5) the compound of term (4), wherein the divalent aromatic monocyclic hydrocarbon group is a phenylene group, (6) the compound of term (1), wherein $R^1$ and $R^2$ are both a chain lower alkyl group, (7) the compound of term (6), wherein the lower alkyl has 1 to 6 carbon atoms, (8) the compound of term (1), wherein $R^1$ and $R^2$ are both ethyl, (9) the compound of term (1), wherein $R^1$ and $R^2$ are both methyl,

(10) the compound of term (1), wherein $R^1$ and $R^2$ are combined together to form —Z— wherein Z represents a carbon chain of a chain length of 2 to 4 atoms that may have at least one side chain,

(11) the compound of term (10), wherein Z is —(CH$_2$)$_3$—,

(12) the compound of term (1), wherein $Q_2$ is hydrogen or a lower alkyl,

(13) the compound of term (1), wherein Y is an alkylene chain,

(14) the compound of term (13), wherein the alkylene chain is —(CH$_2$)$_2$—,

(15) the compound of term (1), wherein the group of the formula —CON(Q₁)(Q₂) is connected to the a-position carbon atom,

(16) the compound of term (1), wherein ring A is substituted by an alkyl group or an aromatic hydrocarbon group,

(17) the compound of term (1), which is one of the formula:

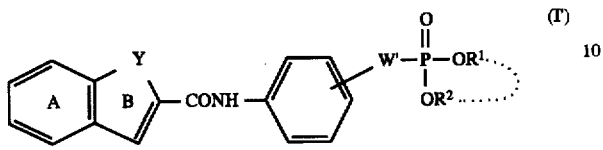

wherein W' is a bond or an alkylene group and the other symbols are as defined in term (1), or a salt thereof,

(18) the compound of term (1), which is 7-cyclohexyl-N-(4-diethoxyphosphorylmethylphenyl)-3,4-dihydronaphthalene-2-carboxamide,

(19) the compound of term (1), which is 7-phenyl-N-(4-diethoxyphosphorylmethylphenyl)-3,4-dihydronaphthalene-2-carboxamide,

(20) the compound of term (1), which is 7-phenyl-N-(4-dimethoxyphosphorylmethylphenyl)-3,4-dihydronaphthalene-2-carboxamide,

(21) a method of producing a compound of the formula:

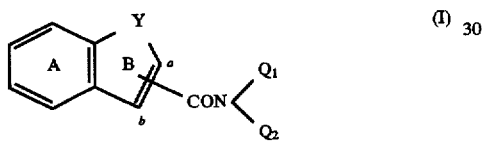

wherein ring A is a benzene ring that may be substituted; Y is a divalent group as a constituent member of ring B forming a 5- to 8-membered ring; Q₁ is a group of the formula:

wherein X is a bond or a divalent group; R¹ and R², identical or different, are hydrogen or a lower alkyl group, or may be combined together to form a ring; Q₂ is hydrogen, a hydrocarbon group that may be substituted or a heterocyclic group that may be substituted; the group represented by the formula —CON(Q₁)(Q₂) is connected to the a- or b-position carbon atom, or a salt thereof, by reacting a compound of the formula:

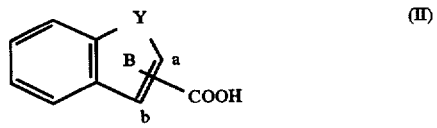

wherein Y is a divalent group as a constituent member of ring B forming a 5- to 8-membered ring; ring A is a benzene ring that may be substituted; the —COOH group is connected to the a- or b-position carbon atom, or a reactive derivative thereof, and a compound of the formula:

wherein Q₁' is a group of the formula:

wherein X represents a bond or a divalent group; R³ and R⁴, identical or different, represent a lower alkyl; Q₂ represents hydrogen, a hydrocarbon group that may be substituted or a heterocyclic group that may be substituted, followed by phosphonate hydrolysis reaction as necessary,

(22) a pharmaceutical composition which comprises a therapeutically effective amount of the compound of term (1) in admixture with a pharmaceutically acceptable carrier, excipient or diluent therefor,

(23) a pharmaceutical composition for promoting osteogenesis which comprises a therapeutically effective amount of the compound of term (1) in admixture with a pharmaceutically acceptable carrier, excipient or diluent therefor,

(24) a pharmaceutical composition for promoting bone fracture healing which comprises a therapeutically effective amount of the compound of term (1) in admixture with a pharmaceutically acceptable carrier, excipient or diluent therefor,

(25) a method for preventing or treating osteoporosis in a mammal which comprises administering to said mammal a therapeutically effective amount of the compound of term (1), and

(26) Use of the compound of term (1) for the manufacture of a medicament to be used as an osteogenesis promoter.

With respect to general formulas (I) [hereinafter including the formula (I')] and (II), ring A may have one or more substituents. Examples of such substituents include halogen atoms, nitro groups, alkyls that may be substituted, hydroxyl groups that may be substituted, thiol groups that may be substituted, amino groups that may be substituted, acyl groups that may be substituted, carboxyl groups that may be esterified, and aromatic ring groups that may be substituted.

The halogen as a substituent for ring A is exemplified by fluorine, chlorine, bromine and iodine, with preference given to fluorine and chlorine.

The alkyl as a substituent for ring A, that may be substituted, is exemplified by alkyls having 1 to 10 carbon atoms, whether linear, branched or cyclic. Linear or branched alkyls include $C_{1-10}$ alkyls such as methyl, ethyl, propyl, isopropyl, butyl, isobutyl, sec-butyl, tert-butyl, pentyl, isopentyl, neopentyl, hexyl, heptyl, octyl, nonyl and decyl, with preference given to lower ($C_{1-6}$) alkyls. Cyclic alkyls include $C_{3-7}$ cycloalkyls such as cyclopropyl, cyclobutyl, cyclopentyl, cyclohexyl and cycloheptyl. Substituents for said alkyl that may be substituted include halogens (e.g., fluorine, chlorine, iodine), nitro groups, hydroxyl groups, thiol groups, amino groups and carboxyl groups.

The hydroxyl group as a substituent for ring A, that may be substituted, is exemplified by hydroxyl group and hydroxyl groups having an appropriate substituent, particularly a substituent for use as a hydroxyl-protecting group, such as alkoxy, alkenyloxy, aralkyloxy and acyloxy, as well as aryloxy. Said alkoxy is preferably an alkoxy having 1 to 10 carbon atoms (e.g., methoxy, ethoxy, propoxy, isopropoxy, butoxy, isobutoxy, sec-butoxy, tert-butoxy, pentyloxy, isopentyloxy, neopentyloxy, hexyloxy, heptyloxy, nonyloxy, cyclobutyloxy, cyclopentyloxy, cyclohexyloxy), more preferably an alkoxy having 1 to 6 carbon atoms. Said alkenyloxy is exemplified by those having 2 to 10 carbon atoms such as allyloxy, crotyloxy, 2-pentenyloxy, 3-hexenyloxy, 2-cyclopentenylmethoxy and 2-cyclohexenylmethoxy. Said aralkyloxy is exemplified by phenyl-$C_{1-4}$ alkyloxys (e.g., benzyloxy, phenethyloxy). Said acyloxy is preferably an alkanoyloxy having 2 to 4 carbon atoms (e.g., acetyloxy, propionyloxy, butyryloxy, isobutyryloxy). Said aryloxy is exemplified by phenoxy and 4-chlorophenoxy.

The thiol group that may be substituted, as a substituent for ring A, is exemplified by thiol group and thiol groups having an appropriate substituent, particularly a substituent for use as a thiol-protecting group, such as alkylthio, aralkylthio and acylthio. Said alkylthio is preferably an alkylthio having 1 to 10 carbon atoms (e.g., methylthio, ethylthio, propylthio, isopropylthio, butylthio, isobutylthio, sec-butylthio, tert-butylthio, pentylthio, isopentylthio, neopentylthio, hexylthio, heptylthio, nonylthio, cyclobutylthio, cyclopentylthio, cyclohexylthio). Said aralkylthio is exemplified by phenyl-$C_{1-4}$ alkylthios (e.g., benzylthio, phenethylthio). Said acylthio is preferably an alkanoylthio having 2 to 4 carbon atoms (e.g., acetylthio, propionylthio, butyrylthio, isobutyrylthio).

Substituents for the amino group that may be substituted, as a substituent for ring A, include chain or cyclic alkyls having 1 to 10 carbon atoms, alkenyl groups having 2 to 10 carbon atoms, aromatic groups and acyl groups; 1 or 2 of these substituents may be present on the amino group (—$NH_2$ group). Such alkyls include $C_{1-10}$ alkyls such as methyl, ethyl, isopropyl, butyl, isobutyl, sec-butyl, tert-butyl, pentyl, isopentyl, neopentyl, hexyl, octyl, nonyl and decyl, with preference given to lower ($C_{1-6}$) alkyls, $C_{3-7}$ cycloalkyls such as cyclopropyl, cyclobutyl, cyclopentyl, cyclohexyl and cycloheptyl, etc. Such alkenyls include allyl, crotyl, 2-pentenyl,o3-hexenyl, 2-cyclopentenylmethyl and 2-cyclohexenylmethyl. Such aromatic groups include phenyl, naphthyl, anthryl and pyridyl. Such acyls include formyl and those resulting from binding of an alkyl having 1 to 10 carbon atoms, alkenyl having 2 to 10 carbon atoms or aromatic group and a carbonyl group, e.g., acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl and nicotinoyl.

The acyl group that may be substituted, as a substituent for ring A, is exemplified by formyl and acyl groups resulting from binding of an alkyl having 1 to 10 carbon atoms, alkenyl having 2 to 10 carbon atoms or aromatic group and a carbonyl group (e.g., acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl, nicotinoyl). Substituents for said acyl group that may be substituted include halogens (e.g., fluorine, chlorine, bromine, iodine), nitro group, hydroxyl group, thiol group, amino group and carboxyl group.

Said ester resulting from esterification of the carboxyl group that may be esterified, as a substituent for ring A, is a lower alkoxycarbonyl group or an aryloxycarbonyl group, with preference given to methoxycarbonyl, ethoxycarbonyl, propoxycarbonyl, phenoxycarbonyl and 1-naphthoxycarbonyl.

The aromatic ring group that may be substituted, as a substituent for ring A, is exemplified by $C_{6-14}$ aromatic hydrocarbon groups such as phenyl, naphthyl and anthryl, and heterocyclic aromatic groups such as pyridyl, furyl, thienyl, imidazolyl and thiazolyl. Substituents for these aromatic ring groups include halogen atoms, nitro group, lower ($C_{1-6}$) alkyls, hydroxyl group, thiol group, amino group and carboxyl group.

One to four of these substituents for such ring A, whether identical or not, may be present at any positions on the ring. Provided that there are mutually adjoining substituents on ring A, they may link together to form a ring represented by —$(CH_2)_m$— or —O—$(CH_2)_n$—O— (m and n respectively represent an integer from 3 to 5, preferably 2 or 3, and an integer from 1 to 3, preferably 1 or 2).

Ring A is preferably a benzene ring having no substituent or a benzene ring substituted by an alkyl group, a halogen atom, an alkoxy group or an aromatic hydrocarbon group.

With respect to the formulas (I), [including (I')] and (II), the divalent group for Y as a constituent member of ring B forming a 5- to 8-membered ring may be any one, as long as ring B forms a 5- to 8-membered ring. Ring B preferably forms a 5- to 7-membered ring. Such divalent groups include divalent groups such as (1) —$(CH_2)_{a_1}$—O—$(CH_2)_{a_2}$— ($a_1$ and $a_2$, whether identical or not, represent 0, 1, 2 or 3, the sum of $a_1$ and $a_2$ being not more than 3), —$(CH_2)_{a_3}$—O—$(CH_2)_{a_4}$—(CH=CH)—$(CH_2)_{a_5}$— or —$(CH_2)_{a_5}$—(CH=CH)—$(CH_2)_{a_4}$—O—$(CH_2)_{a_3}$— ($a_3$, $a_4$ and $a_5$, whether identical or not, represent 0 or 1, the sum of $a_3$, $a_4$ and $a_5$ being not more than 1), —O—(CH=C=CH)— or —(CH=C=CH)—O—, (2) —$(CH_2)_{b_1}$—S—$(CH_2)_{b_2}$— ($b_1$ and $b_2$, whether identical or not, represent 0, 1, 2 or 3, the sum of $b_1$ and $b_2$ being not more than 3), —$(CH_2)_{b_3}$—S—$(CH_2)_{b_4}$—(CH=CH)—$(CH_2)_{b_5}$— or —$(CH_2)_{b_5}$—(CH=CH)—$(CH_2)_{b_4}$—S—$(CH_2)_{b_3}$— ($b_3$, $b_4$ and $b_5$, whether identical or not, represent 0 or 1, the sum of $b_3$, $b_4$ and $b_5$ being not more than 1), —S—(CH=C=CH)— or —(CH=C=CH)—S—, (3) —$(CH_2)_{d_1}$ ($d_1$ represents 1, 2, 3, or 4), —$(CH_2)_{d_2}$—(CH=CH)—$(CH_2)_{d_3}$— ($d_2$ and $d_3$, whether identical or not, represent 0, 1 or 2, the sum of $d_2$ and $d_3$ being not more than 2), —CH=C=CH—, (4) —$(CH_2)_{e_1}$—NH—$(CH_2)_{e_2}$— ($e_1$ and $e_2$, whether identical or not, represent 0, 1, 2 or 3, the sum of $e_1$ and $e_2$ being not more than 3), —$(CH_2)_{e_3}$—NH—$(CH_2)_{e_4}$—(CH=CH)—$(CH_2)_{e_5}$— or —$(CH_2)_{e_5}$—(CH=CH)—$(CH_2)_{e_4}$—NH—$(CH_2)_{e_3}$— ($e_3$, $e_4$ and $e_5$, whether identical or not, represent 0 or 1, the sum of e3, e4 and $e_5$ being not more than 1), —NH—(CH=C=CH)— or —(CH=C=CH)—NH—, —$(CH_2)_{e_6}$—(N=CH)—$(CH_2)_{e_7}$— or —$(CH_2)_{e_7}$—(CH=N)—$(CH_2)_{e_6}$— ($e_6$ and $e_7$, identical or not, represent 0, 1 or 2, the sum of $e_6$ and e7 being not more than 2), —$(CH_2)_{e_8}$—(N=N)—$(CH_2)_{e_9}$— ($e_8$ and e9 whether identical or not, represent 0, 1 or 2, the sum of $e_8$ and $e_9$ being not more than 2). Such divalent groups preferably include divalent groups such as —O—, —O—$CH_2$—, —O—$CH_2$—$CH_2$—, —O—CH=CH—, —S—, —S—$CH_2$—, —S—$CH_2$—$CH_2$—, —S—CH=CH—, alkylene chains represented by —$(CH_2)_k$— (k represents an integer from 1 to 3), —CH=CH—, —CH=CH—$CH_2$—, —$CH_2$—CH=CH—, —NH—, —N=CH—, —CH=N— and —N=N— (each binds to ring A), with preference given to —O—, —O—$CH_2$—, —O—$CH_2$—$CH_2$—, —S—, —S—$CH_2$—, —S—$CH_2$—$CH_2$— or alkylene chains represented by —(CH₂)ₖ— (k represents an integer from 1 to 3), —CH=CH— etc., with greater preference given to —(CH₂)₂— etc. Said divalent group may have one or more substituents; this substituent may be any one, as long as it is capable of binding to the divalent group, and is exemplified by lower (C₁₋₃) alkyls (e.g., methyl, ethyl, propyl), oxo, hydroxy. Said divalent group may also be —O— C(O)— (which binds to ring A), or the like.

With respect to the general formulas (i) and (ii), the divalent group for X is exemplified by those represented by —E—W— (E represents a divalent alicyclic hydrocarbon group, an alicyclic-aliphatic hydrocarbon group, an aromatoaliphatic hydrocarbon group (aralkyl group), an aromatic hydrocarbon group or an aromatic heterocyclic group; W represents a bond or a carbon chain of a chain length of 1 to 4 atoms, that may have at least one substituent). General formulas (i) and (ii) are further represented by general formulas (i') and (ii'), respectively.

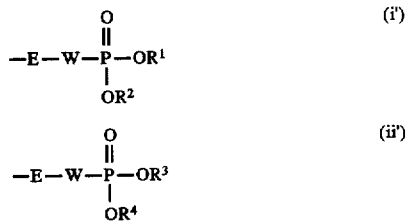

With respect to general formulas (i') and (ii'), the divalent alicyclic hydrocarbon group for E is exemplified by divalent residues derived from saturated alicyclic hydrocarbon groups having 3 to 7 carbon atoms, such as cyclopropyl, cyclobutyl, cyclopentyl, cyclohexyl and cycloheptyl, unsaturated alicyclic hydrocarbon groups having 5 to 7 carbon atoms, such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl and 2,4-cycloheptadienyl, etc.

The alicyclic-aliphatic hydrocarbon group for E is exemplified by groups resulting from binding of an alicyclic hydrocarbon group as described above and an aliphatic hydrocarbon group. The aliphatic hydrocarbon group is exemplified by divalent residues derived from saturated aliphatic hydrocarbon groups having 1 to 8 carbon atoms, such as methyl, ethyl, propyl, isopropyl, butyl, isobutyl, sec-butyl, tert-butyl, pentyl, isopentyl, neopentyl, tert-pentyl, hexyl, isohexyl, heptyl and octyl, unsaturated aliphatic hydrocarbon groups having 2 to 8 carbon atoms, such as ethenyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl and 1-octynyl, etc. Said alicyclic-aliphatic hydrocarbon group is preferably a divalent residue derived from those having 4 to 9 carbon atoms, such as cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl and cycloheptylethyl.

The aromatoaliphatic hydrocarbon group (aralkyl group) for E is exemplified by divalent residues derived from phenylalkyls having 7 to 9 carbon atoms, such as benzyl, phenethyl, 1-phenylethyl, 3-phenylpropyl, 2-phenylpropyl and 1-phenylpropyl, naphthylalkyls having 11 to 13 carbon atoms, such as β-naphthylmethyl, α-naphthylethyl, β-naphthylmethyl and β-naphthylethyl, etc.

The aromatic hydrocarbon group for E is exemplified by divalent groups derived from phenyl, naphthyl (α-naphthyl, β-naphthyl) etc.

The aromatic heterocyclic group for E is exemplified by divalent groups derived from 2-pyridyl, 3-pyridyl, 4-pyridyl, 2-pyrimidinyl, 4-pyrimidinyl, 5-pyrimidinyl, 6-pyrimidinyl, 3-pyridazinyl, 4-pyridazinyl, 2-pyrazinyl, 2-pyrrolyl, 3-pyrrolyl, 2-imidazolyl, 4-imidazolyl, 5-imidazolyl, 3-pyrazolyl, 4-pyrazolyl, isothiazolyl, isoxazolyl, 2-thiazolyl, 4-thiazolyl, 5-thiazolyl, 2-oxazolyl, 4-oxazolyl, 5-oxazolyl, 1,2,4-triazol-3-yl, 1,2,3-triazol-4-yl, tetrazol-5-yl, benzimidazol-2-yl, indol-3-yl, benzopyrazol-3-yl, 1H-pyrrolo[2,3-b]pyrazin-2-yl, 1H-pyrrolo[2,3-b]pyridin-6-yl, 1H-imidazo[4,5-b]pyridin-2-yl, 1H-imidazo[4,5-c]pyridin-2-yl and 1H-imidazo[4,5-b]pyrazin-2-yl.

Also, the divalent group for X is preferably the divalent hydrocarbon group.

With respect to general formula (i'), E may have 1 to 2 substituents at any position(s) thereof, in addition to the group represented by —W—P(O)(OR¹)(OR²). Similarly, E in general formula (ii') may have 1 to 2 substituents at any position(s) thereof, in addition to the group represented by —W—P(O)(OR³)(OR⁴). Such substituents include aliphatic chain hydrocarbon groups, alicyclic hydrocarbon groups, aryl groups, aromatic heterocyclic groups, non-aromatic heterocyclic groups, halogen atoms, nitro groups, amino groups that may be substituted, acyl groups that may be substituted, hydroxyl groups that may be substituted, thiol groups that may be substituted, carboxyl groups that may be esterified, and phosphono groups that may be esterified. Such aliphatic chain hydrocarbon groups include linear or branched aliphatic hydrocarbon groups such as alkyl groups, preferably those having 1 to 10 carbon atoms, alkenyl groups, preferably those having 2 to 10 carbon atoms, and alkinyl groups having 2 to 6 carbon atoms. Such alkyl groups include methyl, ethyl, propyl, isopropyl, butyl, isobutyl, sec-butyl, tert-butyl, pentyl, isopentyl, neopentyl, tert-pentyl, 1-ethylpropyl, hexyl, isohexyl, 1,1-dimethylbutyl, 2,2-dimethylbutyl, 3,3-dimethylbutyl, 2-ethylbutyl, hexyl, pentyl, octyl, nonyl and decyl. Such alkenyl groups include vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl. Such alkinyl groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. Such alicyclic hydrocarbon groups include saturated or unsaturated alicyclic hydrocarbon groups such as cycloalkyl groups, cycloalkenyl groups and cycloalkadienyl groups. Preferable cycloalkyl groups include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2] nonyl, bicyclo[3.3.1]nonyl, bicyclo[4.2.1]nonyl and bicyclo [4.3.1]decyl. Preferable cycloalkenyl groups include 2-cyclopenten-1-yl, 3-cyclopenten-1-yl, 2-cyclohexen-1-yl and 3-cyclohexen-1-yl. Preferable cycloalkadienyl groups include 2,4-cyclopentadien-1-yl, 2,4-cyclohexadien-1-yl and 2,5-cyclohexadien-1-yl. Such aryl groups are monocyclic or condensed polycyclic aromatic hydrocarbon groups, preferably phenyl, naphthyl, anthryl, phenanthryl, acenaphthylenyl and others, with particular preference given to phenyl, 1-naphthyl, 2-naphthyl and others. Preferable aromatic heterocyclic groups include aromatic monocyclic heterocyclic groups such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl, and aromatic condensed heterocyclic groups such as benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthylizinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl and 1,2,4-triazolo[4,3-b]pyridazinyl. Preferable non-aromatic heterocyclic groups include oxylanyl, azetidinyl, oxetanyl, thietanyl, pyrrolidinyl, tetrahydrofuranyl, thiolanyl, piperizinyl, tetrahydropyranyl, morpholinyl, thiomorpholinyl and piperazinyl. Such halogen atoms include atoms of fluorine, chlorine, bromine and iodine, with preference given to fluorine and chlorine. Such amino groups that may be substituted include those resulting from substitution of 1 or 2 of alkyls having 1 to 10 carbon atoms, alkenyls having 2 to 10 carbon atoms, aromatic groups and acyl groups having 2 to 10 carbon atoms for amino group (—NH$_2$ group) (e.g., methylamino, dimethylamino, ethylamino, diethylamino, dibutylamino, diallylamino, cyclohexylamino, phenylamino, N-methyl-N-phenylamino, acetylamino, propionylamino, benzoylamino). Such acyl groups that may be substituted include formyl and those resulting from binding of an alkyl having 1 to 10 carbon atoms, alkenyl having 2 to 10 carbon atoms or aromatic group and a carbonyl group (e.g., acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl, nicotinoyl). Such hydroxyl groups that may be substituted include hydroxyl group and hydroxyl groups having an appropriate substituent, particularly a substituent for use as a hydroxyl-protecting group, such as alkoxy, alkenyloxy, aralkyloxy, acyloxy and aryloxy. Said alkoxy is preferably an alkoxy having 1 to 10 carbon atoms (e.g., methoxy, ethoxy, propoxy, isopropoxy, butoxy, isobutoxy, sec-butoxy, tert-butoxy, pentyloxy, isopentyloxy, neopentyloxy, hexyloxy, heptyloxy, nonyloxy, cyclobutyloxy, cyclopentyloxy, cyclohexyloxy). Said alkenyloxy is exemplified by those having 2 to 10 carbon atoms such as allyloxy, crotyloxy, 2-pentenyloxy, 3-hexenyloxy, 2-cyclopentenylmethoxy and 2-cyclohexenylmethoxy. Said aralkyloxy is exemplified by phenyl-C$_{1-4}$ alkyloxys (e.g., benzyloxy, phenethyloxy). Said acyloxy is preferably an alkanoyloxy having 2 to 4 carbon atoms (e.g., acetyloxy, propionyloxy, butyryloxy, isobutyryloxy). Said aryloxy is exemplified by phenoxy and 4-chlorophenoxy. Said thiol group that may be substituted is exemplified by thiol group and thiol groups having an appropriate substituent, particularly a substituent for use as a thiol-protecting group, such as alkylthio, aralkylthio and acylthio. Said alkylthio is preferably an alkylthio having 1 to 10 carbon atoms (e.g., methylthio, ethylthio, propylthio, isopropylthio, butylthio, isobutylthio, sec-butylthio, tert-butylthio, pentylthio, isopentylthio, neopentylthio, hexylthio, heptylthio, nonylthio, cyclobutylthio, cyclopentylthio, cyclohexylthio). Said aralkylthio is exemplified by phenyl-C$_{1-4}$ alkylthios (e.g., benzylthio, phenethylthio). Said acylthio is preferably an alkanoylthio having 2 to 4 carbon atoms (e.g., acetylthio, propionylthio, butyrylthio, isobutyrylthio). Said ester resulting from esterification of the carboxyl group that may be esterified is exemplified by those resulting from binding of a carboxyl group and an alkyl group having 1 to 6 carbon atoms, such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl, those resulting from binding of a carboxyl group and an alkenyl group having 3 to 6 carbon atoms, such as allyloxycarbonyl, crotyloxycarbonyl, 2-pentenyloxycarbonyl and 3-hexenyloxycarbonyl, and those resulting from binding of a carbonyl group and an aralkyl group, such as benzyloxycarbonyl and phenethyloxycarbonyl. Said phosphono group that may be esterified is exemplified by those represented by P(O)(OR$^5$)(OR$^6$) (R$^5$ and R$^6$ are respectively exemplified by the same examples as those given for R$^1$ and R$^2$ below).

With respect to general formulas (i') and (ii'), substituents for the divalent alicyclic hydrocarbon group, alicyclic-aliphatic hydrocarbon group, aromatoaliphatic hydrocarbon group, aromatic hydrocarbon group or aromatic heterocyclic group for E may further have 1 or more than 1 appropriate substituents, preferably 1 to 3 substituents, at any possible positions. Such substituents include lower (C$_{1-6}$) alkyl groups (e.g., methyl, ethyl, propyl, isopropyl, butyl, isobutyl, sec-butyl, tert-butyl, pentyl, isopentyl, neopentyl, hexyl), lower alkenyl groups (e.g., vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl), lower alkinyl groups (e.g., ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl), cycloalkyl groups (e.g., cyclopropyl, cyclobutyl, cyclopentyl, cyclohexyl, cycloheptyl), aryl groups (e.g., phenyl, 1-naphthyl, 2-naphthyl), aromatic heterocyclic groups, non-aromatic heterocyclic groups, aralkyl groups, amino groups, N-monosubstitutional amino groups (e.g., methylamino, ethylamino, cyclohexylamino, phenylamino), N,N-disubstitutional amino groups (e.g., dimethylamino, diethylamino, dibutylamino, diallylamino, N-methyl-N-phenylamino), amidino groups, acyl groups, carbamoyl groups, N-monosubstitutional carbamoyl groups (e.g., methylcarbamoyl, ethylcarbamoyl, cyclohexylcarbamoyl, phenylcarbamoyl), N,N-disubstitutional carbamoyl groups (e.g., dimethylcarbamoyl, diethylcarbamoyl, dibutylcarbamoyl, diallylcarbamoyl, N-methyl-N-phenylcarbamoyl), sulfamoyl groups, N-monosubstitutional sulfamoyl groups (e.g., methylsulfamoyl, ethylsulfamoyl, cyclohexylsulfamoyl, phenylsulfamoyl), N,N-disubstitutional sulfamoyl groups (e.g., dimethylsulfamoyl, diethylsulfamoyl, dibutylsulfamoyl, diallylsulfamoyl, N-methyl-N-phenylsulfamoyl), carboxyl groups, lower alkoxycarbonyl groups (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl), hydroxyl groups, lower alkoxy groups (e.g., methoxy, ethoxy, propoxy, isopropoxy, butoxy, isobutoxy, sec-butoxy, tert-butoxy, pentyloxy), lower alkenyloxy groups (e.g., allyloxy, crotyloxy, 2-pentenyloxy, 3-hexenyloxy), cycloalkyloxy groups (e.g., cyclopropyloxy, cyclobutyloxy, cyclopentyloxy, cyclohexyloxy, cycloheptyloxy), lower alkylthio groups (e.g., methylthio, ethylthio, propylthio, isopropylthio, butylthio, isobutylthio, sec-butylthio, tert-butylthio, pentylthio, isopentylthio, neopentylthio, hexylthio), aralkylthio groups, arylthio groups, sulfo group, cyano group, azide group, halogen atoms (e.g., fluorine, chlorine, bromine, iodine), nitro group, nitroso group, and phosphono groups that may be esterified. Said aralkyl group is an alkyl group (e.g., methyl, ethyl, propyl, isopropyl, butyl, isobutyl, sec-butyl, tert-butyl, pentyl, isopentyl, neopentyl, hexyl) having an aryl group (e.g., phenyl, 1-naphthyl, 2-naphthyl) as a substituent. Said aralkylthio group is a thiol group having an aralkyl group as a substituent; the aralkyl group is exemplified by the same examples as those given above. Said arylthio group is a thiol group having an aryl group (e.g., phenyl, 1-naphthyl, 2-naphthyl) as a substituent. Said aromatic heterocyclic group, non-aromatic heterocyclic group, acyl, or phosphono group that may be esterified is exemplified by the same examples as those given for substituents for the alicyclic hydrocarbon group, alicyclic-aliphatic hydrocarbon group, aromatoaliphatic hydrocarbon group, aromatic hydrocarbon group or aromatic heterocyclic group for E above.

With respect to general formulas (i') and (ii'), the carbon chain of a chain length of 1 to 4 atoms for W, that may be substituted, may be any one, as long as it is a divalent chain whose linear moiety consists of 1 to 4 atoms. The divalent chain constituting the linear moiety is exemplified by alkylene chains represented by —$(CH_2)_{k1}$— ($k_1$ represents an integer from 1 to 4) and alkenylene chains represented by —$(CH_2)_{k2}$—(CH=CH)—$(CH_2)_{k3}$— ($k_2$ and $k_3$, whether identical or not, represent 0, 1 or 2, the sum of $k_2$ and $k_3$ being not more than 4). Said substituent may be any one, as long as it is capable of binding to the divalent chain constituting the linear moiety. Such substituents include lower alkyls having 1 to 6 carbon atoms (e.g., methyl, ethyl, propyl, isopropyl, butyl, isobutyl, sec-butyl, tert-butyl, pentyl, isopentyl, neopentyl, hexyl), lower ($C_{3-7}$) cycloalkyls (e.g., cyclopropyl, cyclobutyl, cyclopentyl, cyclohexyl, cycloheptyl), phosphono groups that may be esterified, carboxyl groups that may be esterified and hydroxyl group, with preference given to lower alkyls having 1 to 6 carbon atoms, more preferably $C_{1-3}$ alkyls. Said phosphono group that may be esterified is represented by P(O)(OR$^7$)(OR$^8$) (R$^7$ and R$^8$ are respectively exemplified by the same examples as those given for R$^1$ and R$^2$ below). Said ester of the carboxyl group that may be esterified is exemplified by those resulting from binding of a carboxyl group and an alkyl group having 1 to 6 carbon atoms, such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

With respect to general formulas (i) and (ii'), E is preferably a divalent aromatic hydrocarbon group, more preferably a monocyclic aromatic hydrocarbon group (e.g., o-phenylene, m-phenylene, p-phenylene).

With respect to general formulas (i') and (ii'), W is preferably an alkylene chain.

The group of general formula (i') is preferably represented by the formula:

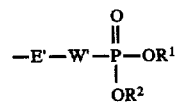

wherein E' represents an aromatic hydrocarbon group; W' represents a bond or an alkylene chain; R$^1$ and R$^2$ have the same definitions as those given below, and is more preferably represented by the formula:

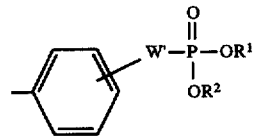

The substitutional position of —W'—P(O)(OR$^1$)(OR$^2$) may be any of the ortho-, meta- and para-positions, but is preferably the para-position.

The group of general formula (ii') is preferably represented by the formula:

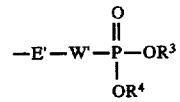

wherein E' represents an aromatic hydrocarbon group; W' represents a bond or an alkylene chain; R$^3$ and R$^4$ have the same definitions as those given below, and is more preferably represented by the formula:

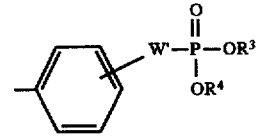

The substitutional position of —W'—P(O)(OR$^3$)(OR$^4$) may be any of the ortho-, meta- and para-positions, but is preferably the para-position.

With respect to general formulas (i) and (i'), the lower alkyl group for R$^1$ or R$^2$ is exemplified by linear or branched lower alkyls having 1 to 6 carbon atoms (e.g., methyl, ethyl, propyl, isopropyl, butyl, isobutyl, sec-butyl, tert-butyl, pentyl, isopentyl, neopentyl, hexyl) and lower ($C_{3-7}$) cycloalkyls (e.g., cyclopropyl, cyclobutyl, 15 cyclopentyl, cyclohexyl, cycloheptyl), with preference given to chain lower alkyls having 1 to 6 carbon atoms, more preferably lower alkyls having 1 to 3 carbon atoms. Although R$^1$ and R$^2$ may be identical or not, it is preferable that they are identical. R$^1$ and R$^2$ may bind together to form a ring; for example, R$^1$ and R$^2$ may bind together to form a ring represented by —Z—(Z represents a carbon chain of a chain length of 2 to 4 atoms that may have a side chain).

With respect to general formulas (ii) and (ii'), the lower alkyl group for R$^3$ or R$^4$ is exemplified by linear or branched lower alkyls having 1 to 6 carbon atoms (e.g., methyl, ethyl, propyl, isopropyl, butyl, isobutyl, sec-butyl, tert-butyl, pentyl, isopentyl, neopentyl, hexyl) and lower ($C_{3-7}$) cycloalkyls (e.g., cyclopropyl, cyclobutyl, cyclopentyl, cyclohexyl, cycloheptyl), with preference given to chain lower alkyls having 1 to 6 carbon atoms, more preferably lower alkyls having 1 to 3 carbon atoms. Although R$^3$ and R$^4$ may be identical or not, it is preferable that they are identical. $R^3$ and $R^4$ may bind together to form a ring; for example, $R^3$ and $R^4$ may bind together to form a ring represented by —Z—(Z represents a carbon chain of a chain length of 2 to 4 atoms that may have a side chain).

Z is exemplified by the same examples as those given for the carbon chain for W but the chain length is 2 to 4 atoms, specifically those resulting from binding of $R^1$ and $R^2$ or $R^3$ and $R^4$, such as —$(CH_2)_2$—, —$(CH_2)_3$—, —$(CH_2)_4$—, —$CH(CH_3)$—$CH_2$—, —$CH(CH_3)$—$CH(CH_3)$—, —$CH_2$—$C(CH_3)_2$—$CH_2$—, —$CH_2$—$CH(C_2H_5)$—$CH_2$— and —CH$(CH_3)$—$CH_2$—$CH(CH_3)$—, preferably —$(CH_2)_2$—, —$(CH_2)_3$—, —$(CH_2)_4$— etc., more preferably —$(CH_2)_3$—. Z may have a side chain. Such side chains include lower alkyls having 1 to 4 carbon atoms (e.g., methyl, ethyl, propyl, isopropyl, butyl, isobutyl, sec-butyl, tert-butyl). The side chain may have one or more substituents; for example, the side chain may be substituted by a hydroxyl group, a halogen, or the like.

With respect to general formulas (I) and (III), the hydrocarbon group for $Q_2$ that may be substituted is an aliphatic hydrocarbon group, an alicyclic hydrocarbon group, an alicyclic-aliphatic hydrocarbon group, an aromatoaliphatic hydrocarbon group (aralkyl group) or an aromatic hydrocarbon group. Said aliphatic hydrocarbon group is exemplified by saturated aliphatic hydrocarbon groups having 1 to 8 carbon atoms, such as methyl, ethyl, propyl, isopropyl, butyl, isobutyl, sec-butyl, tert-butyl, pentyl, isopentyl, neopentyl, tert-pentyl, hexyl, isohexyl, heptyl and octyl, and unsaturated aliphatic hydrocarbon groups having 2 to 8 carbon atoms, such as etenyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, 1-heptenyl, 1-octenyl, etynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl and 1-octynyl, etc. Said alicyclic hydrocarbon group is exemplified by saturated alicyclic hydrocarbon groups having 3 to 7 carbon atoms, such as cyclopropyl, cyclobutyl, cyclopentyl, cyclohexyl and cycloheptyl, and unsaturated alicyclic hydrocarbon groups having 5 to 7 carbon atoms, such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl and 2,4-cycloheptadienyl. Said alicyclic-aliphatic hydrocarbon group is exemplified by groups having 4 to 9 carbon atoms resulting from binding of an alicyclic hydrocarbon group as described above and an aliphatic hydrocarbon group, such as cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl and cycloheptylethyl. Said aromatoaliphatic hydrocarbon group (aralkyl group) is exemplified by phenylalkyls having 7 to 9 carbon atoms, such as benzyl, phenethyl, 1-phenylethyl, 3-phenylpropyl, 2-phenylpropyl and 1-phenylpropyl, naphthylalkyls having 11 to 13 carbon atoms, such as α-naphthylmethyl, α-naphthylethyl, β-naphthylmethyl and β-naphthylethyl, etc. Said aromatic hydrocarbon group is exemplified by phenyl and naphthyl (α-naphthyl, β-naphthyl).

With respect to general formulas (I) and (II), the heterocyclic group for $Q_2$, which may be substituted, is exemplified by 5- to 7-membered heterocyclic ring groups containing 1 atom of sulfur, nitrogen or oxygen, 5- or 6-membered heterocyclic ring groups containing 2 to 4 atoms of nitrogen and 5- or 6-membered heterocyclic groups containing 1 or 2 atoms of nitrogen and 1 atom of sulfur or oxygen. These heterocyclic groups may be condensed with a 6-membered ring containing 2 or fewer atoms of nitrogen, a benzene ring or a 5-membered ring containing 1 atom of sulfur. Said heterocyclic group is preferably an aromatic heterocyclic group, exemplified by 2-pyridyl, 3-pyridyl, 4-pyridyl, 2-pyrimidinyl, 4-pyrimidinyl, 5-pyrimidinyl, 6-pyrimidinyl, 3-pyridazinyl, 4-pyridazinyl, 2-pyrazinyl, 2-pyrrolyl, 3-pyrrolyl, 2-imidazolyl, 4-imidazolyl, 5-imidazolyl, 3-pyrazolyl, 4-pyrazolyl, isothiazolyl, isoxazolyl, 2-thiazolyl, 4-thiazolyl, 5-thiazolyl, 2-oxazolyl, 4-oxazolyl, 5-oxazolyl, 1,2,4-triazol-3-yl, 1,2,3-triazol-4-yl, tetrazol-5-yl, benzimidazol-2-yl, indol-3-yl, benzopyrazol-3-yl, 1H-pyrrolo[2,3-b]pyrazin-2-yl, 1H-pyrrolo[2,3-b]pyridin-6-yl, 1H-imidazo[4,5-b]pyridin-2-yl, 1H-imidazo[4,5-c]pyridin-2-yl and 1H-imidazo[4,5-b]pyrazin-2-yl.

With respect to general formulas (I) and (II) above, the hydrocarbon group or heterocyclic group for $Q_2$ may have 1 to 3 substituents at any position(s) thereof. Such substituents include aliphatic chain hydrocarbon groups, alicyclic hydrocarbon groups, aryl groups, aromatic heterocyclic groups, non-aromatic heterocyclic groups, halogen atoms, nitro groups, amino groups that may be substituted, acyl groups that may be substituted, hydroxyl groups that may be substituted, thiol groups that may be substituted, carboxyl groups that may be esterified, and phosphono groups that may be esterified. Such aliphatic chain hydrocarbon groups include linear or branched aliphatic hydrocarbon groups such as alkyl groups, preferably those having 1 to 10 carbon atoms, alkenyl groups, preferably those having 2 to 10 carbon atoms, and alkinyl groups having 2 to 6 carbon atoms. Such alkyl groups include methyl, ethyl, propyl, isopropyl, butyl, isobutyl, sec-butyl, tert-butyl, pentyl, isopentyl, neopentyl, tert-pentyl, 1-ethylpropyl, hexyl, isohexyl, 1,1-dimethylbutyl, 2,2-dimethylbutyl, 3,3-dimethylbutyl, 2-ethylbutyl, hexyl, pentyl, octyl, nonyl and decyl. Such alkenyl groups include vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl. Such alkinyl groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. Such alicyclic hydrocarbon groups include saturated or unsaturated alicyclic hydrocarbon groups such as cycloalkyl groups, cycloalkenyl groups and cycloalkadienyl groups. Preferable cycloalkyl groups include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl and bicyclo[4.3.1]decyl. Preferable cycloalkenyl groups include 2-cyclopenten-1-yl, 3-cyclopenten-1-yl, 2-cyclohexen-1-yl and 3-cyclohexen-1-yl. Preferable cycloalkadienyl groups include 2,4-cyclopentadien-1-yl, 2,4-cyclohexadien-1-yl and 2,5-cyclohexadien-1-yl. Such aryl groups are monocyclic or condensed polycyclic aromatic hydrocarbon groups, preferably phenyl, naphthyl, anthryl, phenanthryl, acenaphthylenyl and others, with preference given to phenyl, 1-naphthyl, 2-naphthyl and others. Preferable aromatic heterocyclic groups include aromatic monocyclic heterocyclic groups such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4- thiadiazolyl, 1,2,3-triazolyl, 1,2,4-triazolyl, tetrazolyl, pyridyl, pyridazinyl, pyrimidinyl, pyrazinyl and triazinyl, and aromatic condensed heterocyclic groups such as benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthylizinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl and 1,2,4-triazolo[4,3-b]pyridazinyl. Preferable non-aromatic heterocyclic groups include oxylanyl, azetidinyl, oxetanyl, thietanyl, pyrrolidinyl, tetrahydrofuryl, thiolanyl, piperizinyl, tetraohydropyranoyl, morpholinyl, thiomorpholinyl and piperazinyl. Such halogen atoms include fluorine atoms, chlorine atoms, bromine atoms and iodine atoms, with preference given to fluorine and chlorine. Such amino groups that may be substituted include those resulting from substitution of 1 or 2 of alkyls having 1 to 10 carbon atoms, alkenyls having 2 to 10 carbon atoms, aromatic groups and acyl groups having 2 to 10 carbon atoms for amino group (—NH$_2$ group) (e.g., methylamino, dimethylamino, ethylamino, diethylamino, dibutylamino, diallylamino, cyclohexylamino, phenylamino, N-methyl-N-phenylamino, acetylamino, propionylamino, benzoylamino). Such acyl groups that may be substituted include formyl and groups resulting from binding of an alkyl having 1 to 10 carbon atoms, alkenyl having 2 to 10 carbon atoms or aromatic group and a carbonyl group (e.g., acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl, nicotinoyl). Said hydroxyl group that may be substituted is exemplified by hydroxyl group and hydroxyl groups having an appropriate substituent, particularly a substituent for use as a hydroxyl-protecting group, such as alkoxy, alkenyloxy, aralkyloxy, acyloxy and aryloxy. Said alkoxy is preferably an alkoxy having 1 to 10 carbon atoms (e.g., methoxy, ethoxy, propoxy, isopropoxy, butoxy, isobutoxy, sec-butoxy, tert-butoxy, pentyloxy, isopentyloxy, neopentyloxy, hexyloxy, heptyloxy, nonyloxy, cyclobutyloxy, cyclopentyloxy, cyclohexyloxy). Said alkenyloxy is exemplified by those having 1 to 10 carbon atoms such as allyloxy, crotyloxy, 2-pentenyloxy, 3-hexenyloxy, 2-cyclopentenylmethoxy and 2-cyclohexenylmethoxy. Said aralkyloxy is exemplified by phenyl-C$_{1-4}$ alkyloxys (e.g., benzyloxy, phenethyloxy). Said acyloxy is preferably an alkaoyloxy having 2 to 4 carbon atoms (e.g., acetyloxy, propionyloxy, butyryloxy, isobutyryloxy). Said aryloxy is exemplified by phenoxy and 4-chlorophenoxy. Said thiol group that may be substituted is exemplified by thiol group and thiol groups having an appropriate substituent, particularly a substituent for use as a thiol-protecting group, such as alkylthio, aralkylthio and acylthio. Said alkylthio is preferably an alkylthio having 1 to 10 carbon atoms (e.g., methylthio, ethylthio, propylthio, isopropylthio, butylthio, isobutylthio, sec-butylthio, tert-butylthio, pentylthio, isopentylthio, neopentylthio, hexylthio, heptylthio, nonylthio, cyclobutylthio, cyclopentylthio, cyclohexylthio). Said aralkylthio is exemplified by phenyl-C$_{1-4}$ alkylthios (e.g., benzylthio, phenethylthio). Said acylthio is preferably an alkanoylthio having 2 to 4 carbon atoms (e.g., acetylthio, propionylthio, butyrylthio, isobutyrylthio). Said ester resulting from esterification of the carboxyl group that may be esterified is exemplified by those resulting from binding of a carboxyl group and an alkyl group having 1 to 6 carbon atoms, such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl, those resulting from binding of a carboxyl group and an alkenyl group having 3 to 6 carbon atoms, such as allyloxycarbonyl, crotyloxycarbonyl, 2-pentenyloxycarbonyl and 3-hexenyloxycarbonyl, and those resulting from binding of a carbonyl group and an aralkyl group, such as benzyloxycarbonyl and phenethyloxycarbonyl. Said phosphono group that may be esterified is exemplified by those represented by P(O)(OR$^9$)(OR$^{10}$) (R$^9$ and R$^{10}$ are respectively exemplified by the same examples as those given for R$^1$ and R$^2$ above).

With respect to general formulas (I) and (III) above, substituents for the hydrocarbon group or heterocyclic ring group for Q$_2$, that may be substituted, may have 1 or more than 1 appropriate substituents, preferably 1 to 3 substituents, at any possible positions. Such substituents include lower (C$_{1-6}$) alkyl groups (e.g., methyl, ethyl, propyl, isopropyl, butyl, isobutyl, sec-butyl, tert-butyl, pentyl, isopentyl, neopentyl, hexyl), lower alkenyl groups (e.g., vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl), lower alkinyl groups (e.g., ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl), cycloalkyl groups (e.g., cyclopropyl, cyclobutyl, cyclopentyl, cyclohexyl, cycloheptyl), aryl groups (e.g., phenyl, 1-naphthyl, 2-naphthyl), aromatic heterocyclic groups, non-aromatic heterocyclic groups, aralkyl groups, amino group, N-monosubstitutional amino groups (e.g., methylamino, ethylamino, cyclohexylamino, phenylamino), N,N-disubstitutional amino groups (e.g., dimethylamino, diethylamino, dibutylamino, diallylamino, N-methyl-N-phenylamino), amidino group, acyl groups, carbamoyl group, N-monosubstitutional carbamoyl groups (e.g., methylcarbamoyl, ethylcarbamoyl, cyclohexylcarbamoyl, phenylcarbamoyl), N,N-disubstitutional carbamoyl groups (e.g., dimethylcarbamoyl, diethylcarbamoyl, dibutylcarbmoyl, diallylcarbamoyl, N-methyl-N-phenylcarbamoyl), sulfamoyl groups, N-monosubstitutional sulfamoyl groups (e.g., methylsulfamoyl, ethylsulfamoyl, cyclohexylsulfamoyl, phenylsulfamoyl), N,N-disubstitutional sulfamoyl groups (e.g., dimethylsulfamoyl, diethylsulfamoyl, dibutylsulfamoyl, diallylsulfamoyl, N-methyl-N-phenylsulfamoyl), carboxyl groups, lower alkoxycarbonyl groups (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl), hydroxyl group, lower alkoxy groups (e.g., methoxy, ethoxy, propoxy, isopropoxy, butoxy, isobutoxy, sec-butoxy, tert-butoxy, pentyloxy), lower alkenyloxy groups (e.g., allyloxycarbonyl, crotyloxycarbonyl, 2-pentenyloxycarbonyl, 3-hexenyloxycarbonyl), cycloalkyloxy groups (e.g., cyclopropyloxy, cyclobutyloxy, cyclopentyloxy, cyclohexyloxy, cycloheptyloxy), lower alkylthio groups (e.g., methylthio, ethylthio, propylthio, isopropylthio, butylthio, isobutylthio, sec-butylthio, tert-butylthio, pentylthio, isopentylthio, neopentylthio, hexylthio), aralkylthio groups, arylthio groups, sulfo group, cyano group, azide group, halogen atoms (e.g., fluorine, chlorine, bromine, iodine), nitro group, nitroso group, and phosphono groups that may be esterified. Said aralkyl group is an alkyl group (e.g., methyl, ethyl, propyl, isopropyl, butyl, isobutyl, sec-butyl, tert-butyl, pentyl, isopentyl, neopentyl, hexyl) having an aryl group (e.g., phenyl, 1-naphthyl, 2-naphthyl) as a substituent. Said aralkylthio group is a thiol group having an aralkyl group as a substituent; the aralkyl group is exemplified by the same examples as those given above. Said arylthio group is a thiol group having an aryl group (e.g., phenyl, 1-naphthyl, 2-naphthyl) as a substituent. Said aromatic heterocyclic group, non-aromatic heterocyclic group and acyl are exemplified by the same examples as those given for substituents for the hydrocarbon or heterocyclic ring group that may be substituted for $Q_2$. Said phosphono group that may be esterified is represented by $P(O)(OR^{11})(OR^{12})$ ($R^{11}$ and $R^{12}$ are respectively exemplified by the same examples as those given for $R^1$ and $R^2$ above).

With respect to general formulas (I) and (III) above, $Q_2$ is preferably a hydrogen, a lower alkyl having 1 to 6 carbon atoms (e.g., methyl, ethyl, propyl, isopropyl, butyl, isobutyl, sec-butyl, tert-butyl, pentyl, isopentyl, neopentyl, hexyl), a lower ($C_{3-7}$) cycloalkyl (e.g., cyclopropyl, cyclobutyl, cyclopentyl, cyclohexyl, cycloheptyl), or the like, with greater preference given to a hydrogen and lower alkyls having 1 to 6 carbon atoms (more preferably lower alkyls having 1 to 3 carbon atoms).

With respect to general formula (I), the —$CON(Q_1)(Q_2)$ group may be bound to any of the a- and b-positions, but it is preferably bound to the a-position.

The compound of the general formula (I) above is preferably a compound of the general formula (I'):

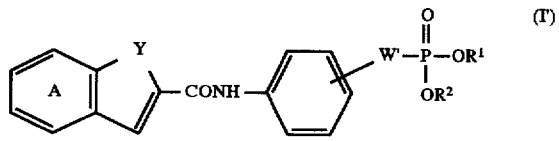

wherein ring A is a benzene ring that may be substituted; Y represents a divalent group as a constituent member of ring B forming a 5- to 7-membered ring; W' represents a bond or an alkylene chain; $R^1$ and $R^2$, whether identical or not, represent a hydrogen or a lower alkyl group, or may bind together to form a ring.

The compound of the present invention is exemplified by 7-cyclohexyl-N-(4-diethoxyphosphorylmethylphenyl)-3,4-dihydronaphthalene-2-carboxamide, 7-cyclohexyl-N-(4-dimethoxyphosphorylmethylphenyl)-3,4-dihydronaphthalene-2-carboxamide, N-(4-diethoxyphosphorylmethylphenyl)naphthalene-2-carboxamide, N-(4-diethoxyphosphorylmethylphenyl)-6,7-methylenedioxy-2-oxochromene-3-carboxamide, 7-cyclohexyl-N-(4-trimethylenedioxyphosphorylmethylphenyl)-3,4-dihydronaphthalene-2-carboxamide, 7-cyclohexyl-N-(4-tetramethylenedioxyphosphorylmethylphenyl)-3,4-dihydronaphthalene-2-carboxamide, N-(4-diethoxyphosphorylmethylphenyl)-3,4-dihydronaphthalene-2-carboxamide, 7-phenyl-N-(4-trimethylenedioxyphosphorylmethylphenyl)-3,4-dihydronaphthalene-2-carboxamide, and 7-phenyl-N-(4-tetramethylenedioxyphosphorylmethylphenyl)-3,4-dihydronaphthalene-2-carboxamide.

The salt of the compound of the present invention, represented by general formula (I) including the general formula (I'), is preferably a pharmacologically acceptable salt, exemplified by salts with inorganic bases, salts with organic bases, salts with inorganic acids, salts with organic acids and salts with basic or acidic amino acids. Preferable salts with inorganic bases include alkali metal salts such as sodium salt and potassium salt, alkaline earth metal salts such as calcium salt and magnesium salt, aluminum salt and ammonium salt. Preferable salts with organic bases include salts with trimethylamine, triethylamine, pyridine, picoline, ethanolamine, diethanolamine, triethanolamine, dicyclohexylamine and N,N'-dibenzylethylenediamine. Preferable salts with inorganic acids include salts with hydrochloric acid, hydrobromic acid, nitric acid, sulfuric acid and phosphoric acid. Preferable salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid and p-toluenesulfonic acid. Preferable salts with basic amino acids include salts with arginine, lysine and ornithine. Preferable salts with acidic amino acids include salts with aspartic acid and glutamic acid.

The compound of the present invention (or salt thereof), represented by general formula (I) (hereinafter referred to briefly as compound (I) including salts thereof and the compounds of the general formula (I') and their salts), can be administered orally or non-orally, singly or as formulated with a pharmacologically acceptable carrier, in the form of solid preparations such as tablets, capsules, granules and powders, or liquid preparations such as syrups and injectable preparations.

Pharmacologically acceptable carriers are various organic or inorganic carrier substances in common use as pharmaceutical materials, including excipients, lubricants, binders and disintegrating agents for solid preparations, and solvents, dissolution aids, suspending agents, isotonizing agents, buffers and soothing agents for liquid preparations. Other pharmaceutical additives such as preservatives, antioxidants, coloring agents and sweetening agents may be used as necessary. Preferable excipients include lactose, sucrose, D-mannitol, starch, crystalline cellulose and light silicic anhydride. Preferable lubricants include magnesium stearate, calcium stearate, talc and colloidal silica. Preferable binders include crystalline cellulose, sucrose, D-mannitol, dextrin, hydroxypropyl cellulose, hydroxypropylmethyl cellulose and polyvinylpyrrolidone. Preferable disintegrating agents include starch, carboxymethyl cellulose, carboxymethyl cellulose calcium, crosscalmellose sodium and carboxymethyl starch sodium. Preferable solvents include water for injection, alcohol, propylene glycol, macrogol, sesame oil and corn oil. Preferable dissolution aids include polyethylene glycol, propylene glycol, D-mannitol, benzyl benzoate, ethanol, tris-aminomethane, cholesterol, triethanolamine, sodium carbonate and sodium citrate. Preferable suspending agents include surfactants such as stearyltriethanolamine, sodium lauryl sulfate, laurylaminopropionic acid, lecithin, benzalkonium chloride, benzethonium chloride and monostearic glycerol, and hydrophilic polymers such as polyvinyl alcohol, polyvinylpyrrolidone, carboxymethyl cellulose sodium, methyl cellulose, hydroxymethyl cellulose, hydroxyethyl cellulose and hydroxypropyl cellulose. Preferable isotonizing agents include sodium chloride, glycerol and D-mannitol. Preferable buffers include buffer solutions of phosphates, acetates, carbonates and citrates. Preferable soothing agents include benzyl alcohol. Preferable preservatives include p-oxybenzoic acid esters, chlorobutanol, benzyl alcohol, phenethyl alcohol, dehydroacetic acid and sorbic acid. Preferable antioxidants include sulfites and ascorbic acid.

The present invention further provides a method of producing the compound (I).

The compound (I) can be produced by known methods, such as those described below. The salts of compounds represented by general formulas (II), (III), (I-1) and (I-2) below are the same as those of compound (I).

And, in each of the below-mentioned reactions, when the starting compound has amino group, carboxyl group or hydroxyl group as the substitutent, it may have a protective group generally used in the peptide chemistry. After completion of the reaction, the target compound can be obtained by removing the protective group upon necessity.

Examples of the amino-protecting group include optionally substituted $C_{1-6}$ alkyl carbonyl (e.g. formyl, methyl carbonyl and ethyl carbonyl), phenyl carbonyl, $C_{1-6}$ alkyl-oxycarbonyl (e.g. methoxycarbonyl and ethoxycarbonyl), phenyloxycarbonyl (e.g. benzoxycarbonyl), $C_{7-10}$ aralkyl-carbonyl (e.g. benzyloxycarbonyl), trityl and phthaloyl. Examples of substituents of them include halogen atoms (e.g. fluoro, chloro, bromo and iodo), $C_{1-6}$ alkyl-carbonyl (e.g. methylcarbonyl, ethylcarbonyl and butylcarbonyl) and nitro group, and the number of the substituents ranges from about 1 to 3.

Examples of the carboxyl-protecting group include $C_{1-6}$ alkyl (e.g. methyl, ethyl, n-propyl, i-propyl, n-butyl and tert-butyl), phenyl, trityl and silyl. Examples of substituents of them include halogen atoms (e.g. fluoro, chloro, bromo and iodo), $C_{1-6}$ alkylcarbonyl (formyl, methylcarbonyl, ethylcarbonyl and butylcarbonyl) and nitro group, and the number of the substituents ranges from about 1 to 3.

Examples of the hydroxyl-protecting group include for example, optionally substituted $C_{1-6}$ alkyl (e.g. methyl, ethyl, n-propyl, i-propyl, n-butyl and tert-butyl), phenyl, $C_{7-10}$ aralkyl (e.g. benzyl), $C_{1-6}$ alkylcarbonyl (e.g. formyl, methylcarbonyl and ethylcarbonyl), phenyloxycarbonyl, $C_{7-10}$ aralkyloxycarbonyl (e.g. benzyloxycarbonyl), pyranyl, furanyl and silyl. As the substituents mentioned above, halogen atoms (e.g. fluoro, chloro, bromo and iodo), $C_{1-6}$ alkyl, phenyl, $C_{7-10}$ aralkyl and nitro group were used. The number of substituents ranges from about 1 to 4.

And, the protecting groups can be introduced or removed by per se known means or those analogous thereto (for example, the method as described in PROTECTIVE GROUPS IN ORGANIC CHEMISTRY (J. F. W. McOmie et al., Plenum Press)). More specifically, those protecting groups are removed by, for example, acid, base, reduction, ultraviolet ray, hydrazine, phenylhydrazine, sodium N-methyldithiocarbamate, tetrabutyl ammonium fluoride or palladium acetate.

Method A

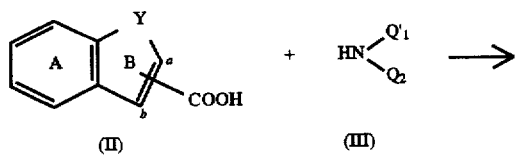

(II)     (III)

-continued

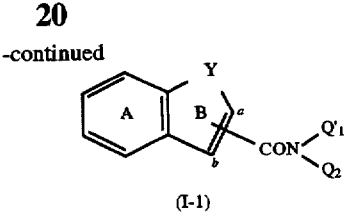

(I-1)

wherein the symbols have the same definitions as those given above.

In this method, compound (I-1) is produced by reacting compound (II) with phosphonate derivative (III).

The condensation reaction of compounds (II) and (III) is carried out by an ordinary means of peptide synthesis. Any optionally chosen known method can be used for this peptide synthesis. Such methods include those described by M. Bodansky and M. A. Ondetti in Peptide Synthesis, Interscience Publishers, New York (1966), by F. M. Finn and K. Hofmann in The Proteins, Vol. 2, edited by H. Nenrath and R. L. Hill, Academic Press Inc., New York (1976), and by Nobuo Izumiya et al. in Peptide Gosei No Kiso To Jikken (in Japanese), Maruzen (1985), respectively known as the azide method, the chloride method, the acid anhydride method, the mixed acid anhydride method, the DCC method, the active ester method, the method using Woodward reagent K, the carbonyldiimidazole method, the oxidation reduction method, the DCC/HONB method, and the method using diethyl phosphorocyanidate (DEPC). This condensing reaction can be carried out in a solvent. The solvent is exemplified by anhydrous or hydrated N,N-dimethylformamide, dimethyl sulfoxide, pyridine, chloroform, dichloromethane, tetrahydrofuran, dioxane, acetonitrile, and appropriate mixtures thereof. Reaction temperature is normally about −20° to 50° C., preferably about −10° to 30° C. Reaction time is normally about 1 to 100 hours, preferably about 2 to 40 hours.

The thus-obtained phosphonate derivative (I-1) can be isolated and purified by known means of separation and purification, such as concentration, concentration under reduced pressure, solvent extraction, crystallization, recrystallization, redissolution and chromatography.

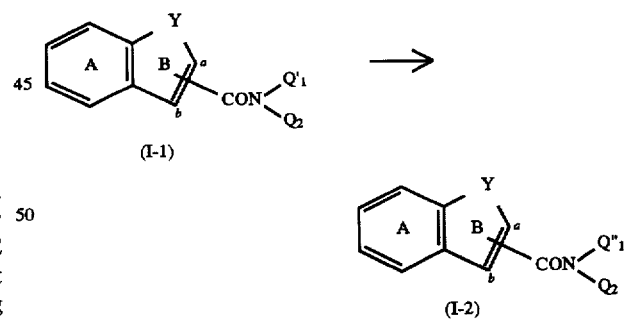

wherein $Q_1''$ represents the formula —X—P(O)(OH)$_2$; the other symbols have the same definitions as those given above.

In this method, phosphonate derivative (I-1) as produced by method A is subjected to a hydrolysis reaction to yield corresponding phosphonic acid (I-2).

This reaction is carried out in a solvent that does not interfere with the reaction, using an inorganic acid such as hydrochloric acid or hydrobromic acid, or a halogenated trialkylsilane.

When an inorganic acid such as hydrochloric acid or hydrobromic acid is used, useful solvents include alcohols such as methanol, ethanol, 2-methoxyethanol, ethylene glycol, propanol and butanol, water, and mixtures thereof. The amount of acid used is normally in excess, reaction temperature being normally about 0° to 150° C., preferably about 30° to 100° C., reaction time being about 1 to 50 hours.

When a halogenated alkylsilane such as chlorotrimethylsilane, bromotrimethylsilane or iodotrimethylsilane is used, useful solvents include halogenated hydrocarbons such as carbon tetrachloride, chloroform, dichloromethane, 1,2-dichloroethane and 1,1,2,2-tetrachloroethane, acetonitrile, and mixtures thereof.

The amount of halogenated alkylsilane used is normally about 1 to 10 equivalents, preferably about 2 to 5 equivalents, per equivalent of compound (I-1). Reaction temperature is normally about −30° to 100° C., preferably about −10° to 50° C., reaction time being about 30 minutes to 100 hours.

The thus-obtained phosphonic acid can be converted into a salt by a conventional treatment with a base such as potassium hydroxide, sodium hydroxide, sodium methoxide, ammonia or organic amine.

The thus-obtained phosphonic acid derivative (I-2) can be isolated and purified by known means of separation and purification, such as concentration, concentration under reduced pressure, solvent extraction, crystallization, recrystallization, redissolution and chromatography.

Starting material compound (II) for method A may be a published known compound as such, or can easily be synthesized by methods described in scientific papers and patent documents [e.g., Organic Synthesis, Vol. 26, p. 28 (1946); Japanese Patent Unexamined Publication No. 230570/1989, Bull. Soc. Chim. Ft., p. 512 (1950); Organic Synthesis, Collective vol. 3, p. 165 (1955)] or modifications thereof. For example, a compound of general formula (II) further represented by general formula (II-1) is produced by methods C-1 and C-2.

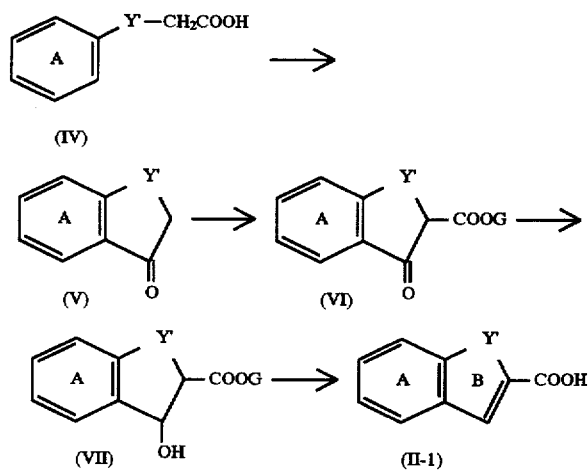

Method C-1

(IV), (V), (VI), (VII), (II-1)

In the above formulas, G represents a lower alkyl group; Y' represents an unsaturated-bond-free divalent group as a constituent member of ring B forming a 5- to 8-membered ring; the other symbols have the same definitions as those given above.

The lower alkyl group for G is exemplified by the same examples of lower alkyl groups as those given for $R^1$ or $R^2$ above but having 1 to 4 carbon atoms.

In this method, a compound of general formula (IV) is first heated in the presence of polyphosphoric acid, or compound (IV) is converted into an acid chloride using thionyl chloride, oxalyl chloride, phosphorus oxychloride, phosphorus pentachloride, or the like, after which it is cyclized by an ordinary process of Friedel-Crafts reaction to yield compound (V). Compound (V) is then reacted with a carbonate in the presence of a base to yield keto ester (VI). Compound (VI) is converted into compound (VII) by catalytic hydrogenation or reduction with sodium borohydride, or the like. After ester hydrolysis reaction, compound (VII) is heated in the presence of an acid to yield unsaturated carboxylic acid (II-1).

Most species of compound (V), that serve as synthesis intermediates for method C, are known in the literature. For example, they are described in the Chemical and Pharmaceutical Bulletin, Vol. 26, p. 504 (1978), the Chemical and Pharmaceutical Bulletin, Vol. 31, p. 2349 (1983), the Chemical and Pharmaceutical Bulletin, Vol. 32, p. 130 (1984), and the Journal of the Agricultural Chemical Society of Japan, Vol. 26, p. 28 (1946). These compounds can be converted into compound (II-1) by method C-1.

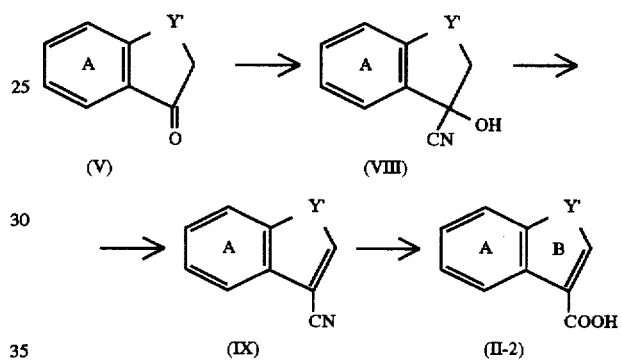

Method C-2

(V), (VIII), (IX), (II-2)

wherein the symbols have the same definitions as those given above.

In this method, a compound of general formula (V) is first converted into cyanohydrin (VIII) by a known method, followed by dehydration reaction, to yield compound (IX). Compound (IX) is subjected to a known acid or alkaline hydrolysis reaction to yield compound (II-2).

Compound (III-1), a compound of general formula (III) having a ring formed cooperatively by $R^3$ and $R^4$ can, for example, be produced by method D.

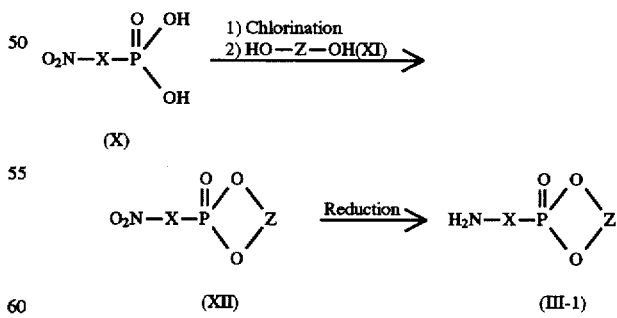

Method D (X), (XII), (III-1)

In the above formulas, the symbols have the same definitions as those given above.

In this method, a compound of general formula (X) is reacted with a chlorinating agent and then reacted with diol (XI) to yield compound (XII). Compound (XII) is then reduced to compound (III-1).

Chlorination of compound (X) is carried out in an appropriate solvent or without solvent. The solvent is exemplified by aromatic hydrocarbons such as benzene, toluene and xylene, ethers such as dioxane, tetrahydrofuran and dimethoxyethane, pyridine, chloroform, dichloromethane, 1,2-dichloroethane, 1,1,2,2-tetrachloroethane, and mixtures thereof. Chlorinating agents include thionyl chloride, oxalyl chloride, phosphorus oxychloride and phosphorus pentachloride, with preference given to thionyl chloride and oxalyl chloride. It is advantageous that this reaction be carried out in the presence of a catalytic amount of N,N-dimethylformamide. Reaction temperature is normally about $-100°$ to $150°$ C., preferably about $-80°$ to $100°$ C. The amount of chlorinating agent used is normally about 1 to 10 mol equivalents, preferably about 1 to 5 mol equivalents per mol equivalent of compound (X). Reaction time is normally about 0.5 to 10 hours. Subsequently, compound (XII) is produced by reaction with diol (XI). This reaction is carried out in an appropriate solvent in the presence of a base. The solvent is exemplified by aromatic hydrocarbons such as benzene, toluene and xylene, ethers such as dioxane, tetrahydrofuran and dimethoxyethane, acetonitrile, chloroform, dichloromethane, 1,2-dichloroethane, 1,1,2,2-tetrachloroethane, and mixtures thereof. The base is exemplified by alkali metal salts such as sodium hydroxide, potassium hydroxide, potassium carbonate, sodium carbonate and sodium hydrogen carbonate, amines such as pyridine, triethylamine and N,N-dimethylaniline, sodium hydride and potassium hydride. The amount of base used is preferably about 1 to 5 mol equivalents per mol equivalent of compound (X). The amount of diol used is preferably about 1 to 5 mol equivalents per mol equivalent of compound (X). This reaction is normally carried out at about $-80°$ to $150°$ C., preferably about $-80°$ to $80°$ C., over a period of about 1 to 50 hours.

The reducing reaction of compound (XII) can be carried out by a known method. Useful methods include reduction with metal hydrides, reduction with metal-hydrogen complex compounds, reduction with diborane or substituted borane, and catalytic hydrogenation. In other words, this reaction is achieved by treating compound (XII) with a reducing agent. Reducing agents include alkali metal borohydrides (e.g., sodium borohydride, lithium borohydride), metal-hydrogen complex compounds such as lithium aluminum hydride, metal hydrides such as sodium hydride, organic tin compounds (e.g., triphenyltin hydride), metals and metal salts such as nickel compounds and zinc compounds, catalytic reducing agents based on a combination of a transient metal such as palladium, platinum or rhodium and hydrogen, and diborane. It is advantageous that this reaction be carried out by catalytic reduction using a combination of a transient metal such as palladium, platinum or rhodium and hydrogen. This reaction is carried out in an organic solvent that does not affect the reaction. Such solvents include aromatic hydrocarbons such as benzene, toluene and xylene, halogenated hydrocarbons such as chloroform, carbon tetrachloride, dichloromethane, 1,2-dichloroethane and 1,1,2,2-tetrachloroethane, ethers such as diethyl ether, tetrahydrofuran and dioxane, alcohols such as methanol, ethanol, propanol, isopropanol and 2-methoxyethanol, amides such as N,N-dimethylformamide, and mixtures thereof, chosen as appropriate for the reducing agent. Reaction temperature is normally about $-20°$ to $150°$ C., preferably about $0°$ to $100°$ C., reaction time being about 1 to 24 hours.

The thus-obtained compound (III-1) can be isolated and purified by known means of separation and purification, such as concentration, concentration under reduced pressure, solvent extraction, crystallization, recrystallization, redissolution and chromatography.

The compound (I) can be used to prevent and treat various metabolic bone diseases, such as osteoporosis, in humans and non-human animals (e.g., mice, rats, cats, dogs, rabbits, bovines, swines) because it potently stimulates osteogenesis. With low toxicity, the compound (I) can be safely used. For example, when the compound of Example 1 below was administered to mice at a dose of 100 mg/kg orally, or at a dose of 50 mg/kg intraperitoneally, no death occurred. Also, when the compound of Example 45 was administered to mice at a dose of 300 mg/kg orally, or at a dose of 200 mg/kg intraperitoneally, no death occurred.

The compound (I) can be used as an osteogenesis stimulator, e.g., a prophylactic/therapeutic agent for osteogenesis (bone formation), or a bone fracture healing promoter.

The compound (I) is administered at a daily dose of 5 to 1,000 mg, preferably 10 to 600 mg, as the active ingredient, depending on patient condition and weight and method of administration, for each adult (weighing 50 kg), in 1 to 3 portions per day, in the case of oral administration.

The compound (I) can be used advantageously to prevent and treat various metabolic bone diseases, such as osteoporosis, in humans and non-human animals because it potently promotes osteogenesis.

BEST MODE FOR CARRYING OUT INVENTION

The present invention is hereinafter described in more detail by means of the following test example, reference examples and working examples, which examples, however, do not by any means limit the invention.

Test Example

Bone formation-stimulating action

Using stromal cells prepared from the femoral bone marrow of a normal rat, alkaline phosphatase activity was determined as an index of osteogenesis. Specifically, stromal cells, prepared from the femoral bone marrow of a 7-week-old male Sprague-Dawley rat according to the method of Maniatopoulos et al. [Cell Tissue Research, Vol. 254, p. 317 (1988)], were cultured in an α-MEM (minimum essential medium) solution containing both dexamethasone ($10^{-7}$M) and β-glycerophosphoric acid ($10^{-2}$M) to form mineralized bone-like tissue in vitro. One week later, the test compound ($10^{-7}$M or $10^{-5}$M) was added to the confluent cells, followed by 10 to 14 more days of culture in the above culture medium. After washing with phosphate buffer, the cells were scraped into with 0.2% Nonidet P-40, sonicated and centrifuged at 3,000 rpm for 10 minutes. The resulting supernatant was used for assay of alkaline phosphatase activity by the method of Lowry et al. [Journal of Biological Chemistry, Vol. 207, p. 19 (1954)]. The values obtained are given in mean±SE in Table 1. The data were statistically analyzed by Student's t-test.

TABLE 1

| Compound (Example Number) | Concentration (M) | Alkaline Phosphatase Activity (nmol p-nitrophenol/min/well) |
|---|---|---|
| (1) Experiment 1 | | |
| Control | Not added | 221.8 ± 14.4 |
| 1 | $10^{-5}$ | 1144.8 ± 51.5** |

TABLE 1-continued

| Compound (Example Number) | Concentration (M) | Alkaline Phosphatase Activity (nmol p-nitrophenol/min/well) |
| --- | --- | --- |
| (2) Experiment 2 | | |
| Control | Not added | 419.2 ± 25.0 |
| 19 | $10^{-5}$ | 1572.3 ± 68.5** |
| (3) Experiment 3 | | |
| Control | Not added | 397.2 ± 32.0 |
| 32 | $10^{-5}$ | 978.3 ± 96.5** |

**$p < 0.01$ vs control

As stated above, the compound (I), exhibits excellent stimulation of expression of the osteoblast phenotype and is useful as a prophylactic/therapeutic drug for metabolic bone diseases, including osteoporosis. Any bone formation-stimulating compound possessing such activity is applicable to the treatment of bone fractures, bone defects, and bone diseases such as osteoarthritis in the field of orthopedics. They are also expected to be effective in the field of dentistry, including repair of periodontal tissue defects due to periodontitis, stabilization of artificial tooth roots, ridge formation and repair of cleft palate.

The room temperature in the below Reference Examples and Examples ranges from about 15° C. to about 25° C.

Reference Example 1

To a suspension of powdered anhydrous aluminum chloride (16.0 g) in 1,2-dichloroethane (160 ml), ethyl succinyl chloride (19.8 g) and then phenylcyclohexane (16.0 g) were added dropwise under ice cooling conditions. After refluxing for 2.5 hours, the reaction mixture was poured into 6N HCl (50 ml), followed by stirring for 1 hour. The organic layer was collected, while the aqueous layer was extracted with dichloromethane. The extract was combined with the organic layer, washed successively with 3N HCl, water and brine, and dried ($MgSO_4$), after which the solvent was evaporated off. The residual oil was subjected to silica gel column chromatography and eluted with ethyl acetate-hexane (1:9, v/v) to yield ethyl 3-(4-cyclohexylbenzoyl)propionate (14.3 g, 50%), which was then recrystallized from hexane to yield colorless prisms having a melting point of 54°–55° C.

Reference Example 2

Ethyl 3-(3,4-dimethylbenzoyl)propionate, as an oil, was obtained by reaction of o-xylene and ethyl succinyl chloride in the same manner as in Reference Example 1.

NMR (δ ppm in $CDCl_3$): 1.26 (3H, t, $J$=7.0 Hz), 2.31 (6H, s), 2.74 (2H, t, $J$=6.7 Hz), 3.28 (2H, t, $J$=6.7 Hz), 4.16 (2H, q, $J$=7.0 Hz), 7.18–7.26 (1H, m), 7.69–7.75 (Reference m)

Reference Example 3

To a solution of ethyl 3-(4-cyclohexylbenzoyl)propionate (19.6 g) in methanol (150 ml), 2N KOH (102 ml) was added, followed by stirring at room temperature for 1.5 hours. The reaction mixture was poured into water (200 ml), acidified with concentrated hydrochloric acid, and extracted with ethyl acetate. The ethyl acetate layer was washed with water and dried ($MgSO_4$), after which the solvent was evaporated off, to yield 3-(4-cyclohexylbenzoyl)propionic acid (10.8 g, 61%), which was then recrystallized from isopropyl ether to yield colorless prisms having a melting point of 140°–141° C.

Reference Example 4

Ethyl 3-(3,4-dimethylbenzoyl)propionate was treated in the same manner as in Reference Example 3 to yield 3-(3,4-dimethylbenzoyl)propionic acid, which was then recrystallized from isopropyl ether to yield colorless prisms having a melting point of 131°–132° C.

Reference Example 5

To a mixture of succinic anhydride (33.02 g), powdered anhydrous aluminum chloride (88.0 g), nitrobenzene (50 ml) and 1,2-dichloroethane (150 ml), isopropylbenzene (40.0 g) was added dropwise under ice cooling conditions. After refluxing for 2 hours, the reaction mixture was poured into ice water; concentrated hydrochloric acid (80 ml) was added, followed by stirring for 1 hour. The organic layer was collected, while the aqueous layer was extracted with dichloromethane. The extract was combined with the organic layer, washed with water, and dried ($MgSO_4$), after which the solvent was evaporated off. The residual crystals were collected by filtration with hexane to yield 3T(4-isopropylbenzoyl)propionic acid (30.9 g, 43%), which was then recrystallized from ethyl acetate-hexane to yield light brown prisms having a melting point of 142°–144° C.

Reference Example 6

A solution of 3-(4-cyclohexylbenzoyl)propionic acid (10.7 g), acetic acid (100 ml) and perchloric acid (2.3 ml) was hydrogenated in the presence of 5% palladium carbon (50% wet, 3.0g) at room temperature under ordinary pressure. After removal of the catalyst by filtration, the filtrate was concentrated under reduced pressure. After water (100 ml) was added, the residue was extracted with ethyl acetate. The ethyl acetate layer was washed with water and brine, and dried ($MgSO_4$), after which the solvent was evaporated off, to yield 4-(4-cyclohexylphenyl)butyric acid (10.4 g, 100%) as an oil.

NMR (δ ppm in $CDCl_3$): 1.35–1.82 (10H, m), 2.00 (2H, t, $J$=7 Hz), 2.35 (2H, t, $J$=7 Hz), 2.47 (1H, broad s), 2.62 (2H, t, $J$=7 Hz), 7.12 (4H, s), 9.06 (1H, broad s)

Reference Example 7

3-(4-Isopropylbenzoyl)propionic acid was subjected to catalytic hydrogenation in the same manner as in Reference Example 6 to yield 4-(4-isopropylphenyl)butyric acid, which was then recrystallized from hexane to yield colorless prisms having a melting point of 50°–51° C.

Reference Example 8

3-(3,4-Dimethylbenzoyl)propionic acid was subjected to catalytic hydrogenation in the same manner as in Reference Example 6 to yield 4-(3,4-dimethylphenyl)butyric acid, which was then recrystallized from dichloromethane-hexane to yield colorless prisms having a melting point of 50°–51° C.

Reference Example 9

To a mixture of 4-(4-cyclohexylphenyl)butyric acid (10.2 g), thionyl chloride (7.4 g) and toluene (50 ml), pyridine (1 drop) was added. After refluxing for 1.5 hours, the solvent was evaporated off under reduced pressure. The residue was dissolved in dichloromethane (20 ml); this solution was added dropwise to a suspension of powdered anhydrous aluminum chloride (8.3 g) in dichloromethane (100 ml) under ice cooling conditions. After stirring at room temperature for 3 hours, the reaction mixture was poured into 1.2N HCl (150 ml), followed by stirring for 30 minutes. The organic layer was collected, while the aqueous layer was extracted with dichloromethane. The extract was combined with the organic layer, succesively washed with water and brine, and dried (MgSO$_4$), after which the solvent was evaporated off. The residual oil was subjected to silica gel column chromatography and eluted with ethyl acetate-hexane (1:10, v/v) to yield 7-cyclohexyl-1-tetralone (9.4 g, 100%) as an oil.

NMR (δ ppm in CDCl$_3$): 1.40–1.79 (10H, m), 2.10 (2H, m), 2.52 (1H, broad s), 2.64 (2H, t, J=6 Hz), 2.92 (2H, t, J=6 Hz), 7.16 (1H, d, J=9 Hz), 7.33 (1H, dd, J=8 & 2 Hz), 7.90 (1H, d, J=2 Hz)

Reference Example 10

4-(4-Isopropylphenyl)butyric acid was treated in the same manner as in Reference Example 9 to yield 7-isopropyl-1-tetralone as an oil.

NMR (δ ppm in CDCl$_3$): 1.25 (6H, d, J=7 Hz), 2.11 (2H, m), 2.64 (2H, t, J=6.8 Hz), 2.89–2.96 (3H, m), 7.18 (1H, d, J=8.0 Hz), 7.35 (1H, dd, J=8.0 & 2.2 Hz), 7.91 (1H, d, J=2.2 Hz)

Reference Example 11

4-(3,4-Dimethylphenyl)butyric acid was treated in the same manner as in Reference Example 9 to yield 6,7-dimethyl-1-tetralone, which was then recrystallized from hexane to yield colorless prisms having a melting point of 47°–48° C.

Reference Example 12

A mixture of 7-cyclohexyl-1-tetralone (9.4 g), sodium methoxide (8.9 g) and dimethyl carbonate (65 ml) was refluxed for 30 minutes in a nitrogen gas stream. After the reaction mixture was cooled, the resulting crystals were collected by filtration and suspended in ethyl acetate (250 ml), followed by addition of 6N HCl (50 ml). The organic layer was collected, while the aqueous layer was extracted with ethyl acetate. The extract was combined with the organic layer, successively washed with water and brine, and dried (MgSO$_4$), after which the solvent was evaporated off, to yield methyl 7-cyclohexyl-1-tetralone-2-carboxylate (8.6 g, 74%) as an oil.

NMR (δ ppm in CDCl$_3$): 1.37–1.80 (10H, m), 2.27–2.77 (4H, m), 2.54 (1H, broad s), 2.80 (3H, m), 2.99 (1H, t, J=6 Hz), 7.10–7.40 (2H, m), 7.65 (0.5H, d, J=2 Hz), 7.89 (0.5H, d, J=2 Hz)

Reference Example 13

7-Isopropyl-1-tetralone was treated in the same manner as in Reference Example 12 to yield methyl 7-isopropyl-1-tetralone-2-carboxylate as an oil.

NMR (δ ppm in CDCl$_3$): 1.21–1.29 (6H, m), 2.35–3.03 (5H, m), 3.61 (¼H, dd, J=10.0 & 5.2 Hz), 3.78 (¾H, s), 3.82 (¾H, s), 7.07–7.92 (3H, m), 12.47 (¾H, s)

Reference Example 14

6,7-Dimethyl-1-tetralone was treated in the same manner as in Reference Example 12 to yield methyl 6,7-dimethyl-1-tetralone-2-carboxylate, which was then recrystallized from ethyl acetate-hexane to yield colorless prisms having a melting point of 80°–81° C.

Reference Example 15

5,7-Dimethyl-1-tetralone was treated in the same manner as in Reference Example 12 to yield methyl 5,7-dimethyl-1-tetralone-2-carboxylate as an oil.

NMR (δ ppm in CDCl$_3$): 2.26 (3H, s), 2.32 (3H, s), 2.30–3.00 (4H, m), 3.58 (½H, dd, J=10.0 & 5.0 Hz), 3.77 (¾H, s), 3.82 (¾H, s), 7.03 (½H, s), 7.20 (½H, s), 7.51 (½H, s), 12.40 (½H, s)

Reference Example 16

Methyl 7-cyclohexyl-1-tetralone-2-carboxylate (8.6 g) was dissolved in dichloromethane (40 ml)-methanol (50 ml). To this solution, sodium borohydride (1.13 g) was added in small portions at room temperature. The reaction mixture was poured into water (80 ml) and extracted with dichloromethane. The dichloromethane layer was successively washed with water and brine, and dried (MgSO$_4$), after which the solvent was distilled off. The residual oil was dissolved in methanol (40 ml), followed by dropwise addition of 2N NaOH (45 ml) at room temperature and stirring for 1 hour. The reaction mixture was washed with ether; the aqueous layer was acidified with concentrated hydrochloric acid and extracted with dichloromethane. The dichloromethane layer was successively washed with water and brine, and dried (MgSO$_4$), after which the solvent was evaporated off. To the residual oil, dioxane (25 ml) and concentrated hydrochloric acid (4.2 ml) were added, followed by stirring at 90° C. for 40 minutes, after which the mixture was concentrated under reduced pressure. After water was added, the residue was extracted with ethyl acetate. The ethyl acetate layer was successively washed with water and brine, and dried (MgSO$_4$), after which the solvent was evaporated off, to yield 7-cyclohexyl-3,4-dihydronaphthalene-2-carboxylic acid (1.57 g, 20%), which was then recrystallized from ethanol to yield colorless prisms having a melting point of 179°–180° C.

Reference Example 17

Methyl 7-isopropyl-1-tetralone-2-carboxylate was treated in the same manner as in Reference Example 16 to yield 7-isopropyl-3,4-dihydronaphthalene-2-carboxylic acid, which was then recrystallized from ethyl acetate-hexane to yield colorless needles having a melting point of 160°–162° C.

Reference Example 18

Methyl 6,7-dimethyl-1-tetralone-2-carboxylate was treated in the same manner as in Reference Example 16 to yield 3,4-dihydro-6,7-dimethylnaphthalene-2-carboxylic acid, which was then recrystallized from chloroform-hexane to yield colorless prisms having a melting point of 222°–223° C.

Reference Example 19

Methyl 5,7-dimethyl-1-tetralone-2-carboxylate was treated in the same manner as in Reference Example 16 to yield 3,4-dihydro-5,7-dimethylnaphthalene-2-carboxylic acid, which was then recrystallized from ethyl acetate-hexane to yield colorless needles having a melting point of 194°–195° C.

Reference Example 20

A mixture of 4-nitrobenzylphosphonic acid (37.40 g), thionyl chloride (150 ml) and N,N-dimethylformamide (5 drops) was refluxed for 5 hours and then concentrated under reduced pressure. The residue was dissolved in tetrahydrofuran (500 ml); to this solution, a solution of ethylene glycol (10.69 g) in acetonitrile (90 ml) was added dropwise at −78° C. over a period of 15 minutes. Pyridine (28.61 g) was then added dropwise at the same temperature over a period of 15 minutes; the mixture was stirred at room temperature for 15 hours. After the insoluble substance was filtered off, the filtrate was concentrated under reduced pressure; the residue was dissolved in chloroform (400 ml). The insoluble substance previously filtered off was partitioned between water (800 ml) and chloroform (200 ml); the chloroform layer was collected. The above residue solution was combined with the chloroform layer, successively washed with 1N HCl, water, saturated aqueous solution of sodium hydrogen carbonate, water and brine, and dried ($MgSO_4$). The mixture was treated with activated charcoal and the solvent was evaporated off, to yield 2-(4-nitrobenzyl)-1,3,2-dioxaphosphoran-2-oxide (8.86 g, 21%), which was then recrystallized from ethanol-hexane to yield colorless plates having a melting point of 144°–145° C.

Reference Example 21

Oxalyl chloride (22.09 g) was added dropwise to a mixture of 4-nitrobenzylphosphonic acid (17.99 g), pyridine (13.76 g) and tetrahydrofuran (500 ml) at –78° C. After this mixture was stirred at –78° C. for 30 minutes and then at room temperature for 1.5 hours, the insoluble solid was filtered off. The filtrate was concentrated under reduced pressure; the residual oil was dissolved in tetrahydrofuran (500 ml). To this solution, a solution of 1,3-propanediol (2.58 g) in acetonitrile (30 ml) was added dropwise at –78° C. over a period of 15 minutes. Pyridine (5.62 g) was then added dropwise at the same temperature over a period of 5 minutes; the mixture was stirred at room temperature for 15 hours. After the insoluble substance was filtered off, the filtrate was concentrated under reduced pressure. The residue was subjected to silica gel column chromatography and eluted with ethyl acetate-chloroform-methanol (10:10:1, v/v) to yield 2-(4-nitrobenzyl)-1,3,2-dioxaphosphorinan-2-oxide (5.62 g, 26%), which was then recrystallized from ethanol-hexane to yield colorless needles having a melting point of 144°–145° C.

Reference Example 22

4-Nitrobenzylphosphonic acid and 2,2-dimethyl-1,3-propanediol were treated in the same manner as in Reference Example 20 to yield 5,5-dimethyl-2-(4-nitrobenzyl)-1,3,2-dioxaphosphorinan-2-oxide, which was then recrystallized from ethanol-hexane to yield colorless plates having a melting point of 176°–177° C.

Reference Example 23

4-Nitrobenzylphosphonic acid and 2,4-pentanediol were treated in the same manner as in Reference Example 20 to yield 4,6-dimethyl-2-(4-nitrobenzyl)-1,3,2-dioxaphosphorinan-2-oxide, which was then recrystallized from ethanol-hexane to yield colorless needles having a melting point of 152°–153° C.

Reference Example 24

4-Nitrobenzylphosphonic acid and 1,4-butanediol were treated in the same manner as in Reference Example 20 to yield 2-(4-nitrobenzyl)-1,3,2-dioxaphosphepan-2-oxide, which was then recrystallized from ethanol-hexane to yield colorless needles having a melting point of 136°–137° C.

Reference Example 25

4-Nitrobenzylphosphonic acid and 2-methyl-1,3-propanediol were treated in the same manner as in Reference Example 20 to yield 5-methyl-2-(4-nitrobenzyl)-1,3,2-dioxaphosphorinan-2-oxide, which was then recrystallized from ethanol-hexane to yield colorless prisms having a melting point of 170°–171° C.

Reference Example 26

4-Nitrobenzylphosphonic acid and 2-ethyl-2-methyl-1,3-propanediol were treated in the same manner as in Reference Example 20 to yield 5-ethyl-5-methyl-2-(4-nitrobenzyl)-1,3,2-dioxaphosphorinan-2-oxide, which was then recrystallized from ethanol-hexane to yield colorless prisms having a melting point of 184°–185° C.

Reference Example 27

4-Nitrobenzylphosphonic acid and 2,2-diethyl-1,3-propanediol were treated in the same manner as in Reference Example 20 to yield 5,5-diethyl-2-(4-nitrobenzyl)-1,3,2-dioxaphosphorinan-2-oxide, which was then recrystallized from ethanol-hexane to yield colorless prisms having a melting point of 159°–160° C.

Reference Example 28

4-Nitrobenzylphosphonic acid and 2-butyl-2-ethyl-1,3-propanediol were treated in the same manner as in Reference Example 20 to yield 5-butyl-5-ethyl-2-(4-nitrobenzyl)-1,3,2-dioxaphosphorinan-2-oxide, which was then recrystallized from ethanol-hexane to yield colorless prisms having a melting point of 111°–112° C.

Reference Example 29

A solution of 2-(4-nitrobenzyl)-1,3,2-dioxaphosphoran-2-oxide (8.56 g) in methanol (300 ml) was hydrogenerated in the presence of 5% palladium-carbon (50% wet, 4.0 g) at room temperature under ordinary pressure. After removal of the catalyst by filtration, the filtrate was concentrated under reduced pressure to yield 2-(4-aminobenzyl)-1,3,2-dioxaphosphoran-2-oxide (4.25 g, 57%), which was then recrystallized from ethanol-hexane to yield colorless prisms having a melting point of 183°–184° C.

Reference Example 30

2-(4-Nitrobenzyl)-1,3,2-dioxaphosphorinan-2-oxide was subjected to catalytic hydrogenation in the same manner as in Reference Example 29 to yield 2-(4-aminobenzyl)-1,3,2-dioxaphosphorinan-2-oxide, which was then recrystallized from ethanol-hexane to yield colorless needles having a melting point of 172°–173° C.

Reference Example 31

5,5-Dimethyl-2-(4-nitrobenzyl)-1,3,2-dioxaphosphorinan-2-oxide was subjected to catalytic hydrogenation in the same manner as in Reference Example 29 to yield 2-(4-aminobenzyl)-5,5-dimethyl-1,3,2-dioxaphosphorinan-2-oxide, which was then recrystallized from ethanol-hexane to yield colorless needles having a melting point of 152°–153° C.

Reference Example 32

4,6-Dimethyl-2-(4-nitrobenzyl)-1,3,2-dioxaphosphorinan-2-oxide was subjected to catalytic hydrogenation in the same manner as in Reference Example 29 to yield 2-(4-aminobenzyl)-4,6-dimethyl-1,3,2-dioxaphosphorinan-2-oxide, which was then recrystallized from ethanol-hexane to yield colorless prisms having a melting point of 160°–161° C.

Reference Example 33

2-(4-Nitrobenzyl)-1,3,2-dioxaphosphepan-2-oxide was subjected to catalytic hydrogenation in the same manner as in Reference Example 29 to yield 2-(4-aminobenzyl)-1,3,2-dioxaphosphepan-2-oxide, which was then recrystallized from ethanol-hexane to yield colorless prisms having a melting point of 128°–129° C.

Reference Example 34

5-Methyl-2-(4-nitrobenzyl)-1,3,2-dioxaphosphorinan-2-oxide was subjected to catalytic hydrogenation in the same manner as in Reference Example 29 to yield 2-(4-aminobenzyl)-5-methyl-1,3,2-dioxaphosphorinan-2-oxide, which was then recrystallized from ethanol-hexane to yield colorless needles having a melting point of 158°–159° C.

Reference Example 35

5-Ethyl-5-methyl-2-(4-nitrobenzyl)-1,3,2-dioxaphosphorinan-2-oxide was subjected to catalytic hydrogenation in the same manner as in Reference Example 29 to yield 2-(4-aminobenzyl)-5-ethyl-5-methyl-1,3,2-dioxaphosphorinan-2-oxide, which was then recrystallized from ethanol-hexane to yield colorless needles having a melting point of 130°–131° C.

Reference Example 36

5,5-Diethyl-2-(4-nitrobenzyl)-1,3,2-dioxaphosphorinan-2-oxide was subjected to catalytic hydrogenation in the same manner as in Reference Example 29 to yield 2-(4-aminobenzyl)-5,5-diethyl-1,3,2-dioxaphosphorinan-2-oxide, which was then recrystallized from ethanol-hexane to yield colorless prisms having a melting point of 128°–129° C.

Reference Example 37

5-Butyl-5-ethyl-2-(4-nitrobenzyl)-1,3,2-dioxaphosphorinan-2-oxide was subjected to catalytic hydrogenation in the same manner as in Reference Example 29 to yield 2-(4-aminobenzyl)-5-butyl-5-ethyl-1,3,2-dioxaphosphorinan-2-oxide, which was then recrystallized from ethanol-hexane to yield colorless prisms having a melting point of 90°–91° C.

Reference Example 38

To a mixture of sesamol (8.28 g), ethyl orthoformate (53.58 g) and benzene (120 ml), powdered anhydrous aluminum chloride (12.0 g) was added, followed by stirring at room temperature for 1 hour. The mixture was then poured into 5% hydrochloric acid (180 ml) and stirred at room temperature for 30 minutes. After the insoluble substance was filtered off, the filtrate was extracted with ether. The ether layer was washed with water and dried ($MgSO_4$), after which the solvent was evaporated off. The residue was subjected to silica gel column chromatography and eluted with ethyl acetate-hexane (1:8, v/v) to yield 2-hydroxy-4,5-methylenedioxybenzaldehyde (3.48 g, 35%) having a melting point of 128°–129° C.

Reference Example 39

A mixture of 2-hydoxy-4,5-methylenedioxybenzaldehyde (1.16 g), diethyl malonate (1.34 g), piperidine (0.3 g), acetic acid (0.035 ml) and ethanol (30 ml) was refluxed for 4 hours. After the reaction mixture was cooled, the resulting crystal was collected by filtration to yield ethyl 6,7-methylenedioxy-2-oxo-1-benzopyran-3-carboxylate (1.29 g, 70%) having a melting point of 200°–201° C.

Reference Example 40

To a suspension of ethyl 6,7-methylenedioxy-2-oxo-1-benzopyran-3-carboxylate (0.26 g) in methanol (20 ml), 2N KOH (1.5 ml) was added, followed by stirring at room temperature for 2 hours. The reaction mixture was poured into water and acidified with hydrochloric acid; the resulting crystal was collected by filtration to yield 6,7-methylenedioxy-2-oxo-1-benzopyran-3-carboxylic acid (0.1 g, 44%), which was then recrystallized from N,N-dimethylformamide-water to yield yellow prisms having a melting point of 279°–280° C.

Reference Example 41

Sodium borohydride (0.24 g) was added to a mixture of 5-nitro-2-thiophenecarboxaldehyde (1.0 g) and ethanol (30 ml) at 0° C. and then this mixture was stirred at the same temperature for 40 minutes. The reaction mixture was poured into water and extracted with dichloromethane. The dichloromethane layer was washed with water and dried ($MgSO_4$), after which the solvent was evaporated off, to yield 2-hydroxymethyl-5-nitrothiophene (0.5 g, 49%).

NMR($\delta$ ppm in $CDCl_3$): 2.75(1H,br s), 4.88(2H,d,J=5.2 Hz), 6.93(1H,d,J=4.2 Hz),7.81(1H,d,J=4.2 Hz).

Reference Example 42

Phosphorus tribromide ($PBr_3$) (10.45 g) was added dropwise to a mixture of 2-hydroxymethyl-5-nitrothiophene (17.7 g) and toluene (150 ml) and this mixture was stirred at 70° C. for 1.5 hours. The reaction mixture was poured into water and extracted with ether. The ether layer was washed with water and dried ($MgSO_4$), after which the solvent was evaporated off. The residual oil was subjected to solica gel column chromatography and eluted with chloroform to yield 2-bromomethyl-5-nitrothiophene (22.43 g, 92%) as an oil.

NMR($\delta$ ppm in $CDCl_3$): 4.63(2H,s), 7.07(1H,d,J=4.2 Hz), 7.78(1H,d,J=4.2 Hz).

Reference Example 43

A mixture of 2-bromomethyl-5-nitrothiophene (10.0 g) and triethylphosphite (($C_2H_5O)_3P$)) (8.49 ml) was stirred for 3 hours under reflux. The reaction mixture was concentrated under reduced pressure. The residue was subjected to silica gel column chromatography and eluted with chloroform-methanol (10:1, v/v) to yield 2-diethoxyphosporylmethyl-5-nitrothiophene (11.91 g, 95%) as an oil.

NMR($\delta$ ppm in $CDCl_3$): 1.27–1.38(6H,m), 3.36(2H,d, J=21.6 Hz), 4.05–4.21(4H,m), 6.95–6.99(1H,m), 7.79–7.82 (1H,m).

Reference Example 44

2-Diethoxyphosphorylmethyl-5-nitrothiophene was subjected to catalytic hydrogenation in the same manner as in Reference Example 29 to yield 5-amino-2-diethoxyphosphorylmethylthiophene as an oil.

NMR($\delta$ ppm in $CDCl_3$): 1.29(6H,t,J=7 Hz), 3.18(2H,d, J=20.2 Hz), 3.40–3.90(2H,br s), 4.06(2H,q,J=7 Hz), 4.10 (2H,q,J=7 Hz), 6.04(1H,d,J=3.4 Hz), 6.52(1H,m).

Reference Example 45

1-Bromomethyl-4-nitronaphthalene and trimethylphosphite (($CH_3O)_3P$) were treated in the same manner as in

Reference Example 43 to yield dimethyl (4-nitro-1-naphthyl)methylphosphonate, which was then recrystallized from ethanol-hexane to yield yellow prisms having a melting point of 128°–129° C.

Reference Example 46

Dimethyl (4-nitro-1-naphthyl)methylphosphonate was subjected to catalytic hydrogenation in the same manner as in Reference Example 29 to yield dimethyl (4-amino-1-naphthyl)methylphosphonate as an oil.

NMR(δ ppm in CDCl$_3$): 3.23(2H,br s), 3.55(2H,d,J=22 Hz), 3.55(3H,s), 3.61(3H,s), 6.75(1H,dd,J=8&1 Hz), 7.28 (1H,dd,J=8&4 Hz), 7.43–7.58(2H,m), 7.82–7.87(1H,m), 8.00–8.05(1H,m).

Reference Example 47

1-Bromomethyl-4-nitronaphthalene and triethylphosphite ((C$_2$H$_5$O)$_3$P) were treated in the same manner as in Reference Example 43 to yield diethyl (4-amino-1-naphthyl) methylphosphonate, which was then recrystallized from ethyl acetate-hexane to yield yellow prisms having a melting point of 73°–74° C.

Reference Example 48

Diethyl (4-nitro-1-naphthyl)methylphosPhonate was subjected to catalytic hydrogenation in the same manner as in Reference Example 29 to yield diethyl (4-amino-1-naphthyl)methylphosphonate as an oil.

NMR(δ ppm in CDCl$_3$): 1.15(6H,t,J=7 Hz), 3.39(2H,br s), 3.53(2H,d,J=21 Hz), 3.83–3.98(4H,m), 6.74(1H,dd, J=8&1 Hz), 7.28(1H,dd,J=8&4 Hz), 7.41–7.57(2H,m), 7.81–7.86(1H,m), 8.03–8.08(1H,m).

Reference Example 49

2-Bromomethyl-5-nitrothiophene and trimethylphosphite ((CH$_3$O)$_3$P) were treated in the same manner as in Reference Example 43 to yield 2-dimethoxyphosphorylmethyl-5-nitrothiophene as an oil.

NMR(δ ppm in CDCl$_3$): 3.38(2H,d,J=22 Hz), 3.76(3H,s), 3.81(3H,s), 6.95–6.99(1H,m), 7.79–7.81(1H,m).

Reference Example 50

2-Dimethoxyphosphorylmethyl-5-nitrothiophene was subjected to catalytic hydrogenation in the same manner as in Reference Example 29 to yield 5-amino-2-dimethoxyphosphorylmethylthiophene as an oil.

NMR(δ ppm in CDCl$_3$): 3.20(2H,d,J=20 Hz), 3.70(3H,s), 3.76(3H,s), 6.03–6.05(1H,m), 6.51–6.54(1H,m).

Reference Example 51

Tert-butylbenzene and ethyl succinyl chloride were treated in the same manner as in Reference Example 1 to yield ethyl 4-(4-tert-butylphenyl)-4-oxobutyrate as an oil.

NMR(δ ppm in CDCl$_3$): 1.27(3H,t,J=7 Hz), 1.34(9H,s), 2.75(2H,t,J=6.6 Hz), 3.30(2H,t,J=6.6 Hz), 4.16(2H,q,J=7 Hz), 7.48(2H,d,J=8 Hz), 7.93(2H,d,J=8 Hz).

Reference Example 52

Ethyl 4-(4-tert-butylphenyl)-4-oxobutyrate was subjected to a hydrolysis reaction in the same manner as in Reference Example 3 to yield 4-(4-tert-butylphenyl)-4-oxobutyric acid, which was then recrystallized from ethyl acetate-hexane to yield light brown prisms having a melting point of 124°–125° C.

Reference Example 53

4-(4-Tert-butylphenyl)-4-oxobutyric acid was subjected to catalytic hydrogenation in the same manner as in Reference Example 6 to yield 4-(4-tert-butylphenyl)butyric acid, which was then recrystallized from hexane to yield colorless prisms having a melting point of 58°–59° C.

Reference Example 54

4-(4-Tert-butylphenyl)butyric acid was treated in the same manner as in Reference Example 9 to yield 7-tert-butyl-1-tetralone, which was then recrystallized from isopropyl ether to yield colorless prisms having a melting point of 101°–102° C.

Reference Example 55

7-Tert-butyl-1-tetralone was treated in the same manner as in Reference Example 12 to yield methyl 7-tert-butyl-1-tetralone-carboxylate as an oil.

NMR(δ ppm in CDCl$_3$): 1.32(2.7H,s), 1.34(6.3H,s), 2.29–2.60(2H,m), 2.74–3.03(2H,m), 3.61(0.3H,dd,J=10&5 Hz), 3.79(0.9H,s), 7.11(0.7H,d,J=8 Hz), 7.19(0.3H,d,J=8 Hz), 7.37(0.7H,dd,J=8&2 Hz), 7.55(0.3H,dd,J=8&2.2 Hz), 7.84(0.7H,d,J=2 Hz), 8.06(0.3H,d,J=2.2 Hz), 12.49(0.7H,s).

Reference Example 56

Methyl 7-tert-butyl-1-tetralone-carboxylate was treated in the same manner as in Reference Example 16 to yield 3,4-dihydro-7-tert-butylnaphthalene-2-carboxylic acid, which was then recrystallized from isopropyl ether to yield colorless prisms having a melting point of 185°–186° C.

Reference Example 57

Biphenyl and ethyl succinyl chloride were treated in the same manner as in Reference Example 1 to yield ethyl 4-(4-phenylphenyl)-4-oxobutyrate, which was then recrystallized from ethyl acetate-hexane to yield yellow prisms having a melting point of 100°–101° C.

Reference Example 58

Ethyl 4-(4-phenylphenyl)-4-oxobutyrate was subjected to a hydrolysis reaction in the same manner as in Reference Example 3 to yield 4-(4-phenylphenyl)-4-oxobutyric acid, which was then recrystallized from ethyl acetate-hexane to yield colorless prisms having a melting point of 187°–189° C.

Reference Example 59

4-(4-Phenylphenyl)-4-oxobutyric acid was subjected to catalytic hydrogenation in the same manner as in Reference Example 6 to yield 4-(4-phenylphenyl)butyric acid, which was then recrystallized from ethyl acetate-hexane to yield colorless prisms having a melting point of 120°–121° C.

Reference Example 60

4-(4-Phenylphenyl)butyric acid was treated in the same manner as in Reference Example 9 to yield 7-phenyl-1-tetralone, which was then recrystallized from isopropyl ether to yield colorless prisms having a melting point of 68°–69° C.

Reference Example 61

7-Phenyl-1-tetralone was treated in the same manner as in Reference Example 12 to yield methyl 7-phenyl-1-tetralone-2-carboxylate as an oil.

NMR(δ ppm in CDCl₃): 2.35–2.64(2H,m), 2.86(1.4H,t, J=8 Hz), 3.00–3.15(0.6H,m), 3.67(0.3H,dd,J=10&4.8 Hz), 3.80(0.9H,s), 3.84(2.1H,s), 7.23–7.77(7H,m), 8.06(0.7H,dd, J=1.6 Hz), 8.30(0.3H,d,J=1.8 Hz), 12.48(0.7H,s).

Reference Example 62

Methyl 7-Phenyl-1-tetralone-2-carboxylate was treated in the same manner as in Reference Example 16 to yield 3,4-dihydro-7-phenylnaphthalene-2-carboxylic acid, which was then recrystallized from ethanol to yield colorless prisms having a melting point of 208°–209° C.

Reference Example 63

Indane and ethyl succinyl chloride were treated in the same manner as in Reference Example 1 to yield ethyl 4-(5-indanyl)-4-oxobutyrate, which was then recrystallized from isopropyl ether to yield colorless prisms having a melting point of 51°–52° C.

Reference Example 64

Ethyl 4-(5-indanyl)-4-oxobutyrate was subjected to a hydrolysis reaction in the same manner as in Reference Example 3 to yield 4-(5-indanyl)-4-oxobutyric acid, which was then recrystallized from ethyl acetate-hexane to yield colorless needles having a melting point of 125°–126° C.

Reference Example 65

4-(5-Indanyl)-4-oxobutyric acid was subjected to catalytic hydrogenation in the same manner as in Reference Example 6 to yield 4-(5-indanyl)butyric acid, which was then recrystallized from hexane to yield colorless prisms having a melting point of 57°–58° C.

Reference Example 66

4-(5-Indanyl)butyric acid was treated in the same manner as in Reference Example 9 to yield 2,3,5,6,7,8-hexahydro-1H-benzo[f]indene-5-on (see the following formula) as an oil.

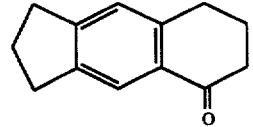

NMR(δ ppm in CDCl₃): 2.00–2.16(4H,m), 2.59–2.66(2H, m), 2.87–2.95(6H,m), 7.10(1H,s), 7.89(1H,s).

Reference Example 67

2,3,5,6,7,8-Hexahydro-1H-benzo[f]indene-5-on was treated in the same manner as in Reference Example 12 to yield methyl 2,3,5,6,7,8-hexahydro-5-oxo-1H-benzo[f]indene-6-carboxylate (see the following formula), which was then recrystallized from hexane to yield colorless prisms having a melting point of 73°–75° C.

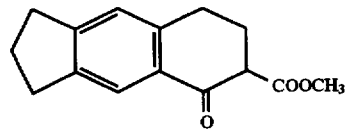

Reference Example 68

Methyl 2,3,5,6,7,8-hexahydro-5-oxo-1H-benzo[f]indene-6-carboxylate was treated in the same manner as in Reference Example 16 to yield 2,3,5,6-tetrahydro-1H-benzo[f]indene-7-carboxylic acid (see the following formula), which was then recrystallized from ethyl acetate to yield colorless crystals having a melting point of 227°–228° C.

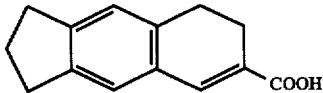

EXAMPLE 1

To a solution off 7-cyclohexyl-3,4-dihydronaphthalene-2-carboxylic acid (0.51 g) in N,N-dimethylformamide (DMF) (15 ml), diethyl phosphorocyanidate (DEPC) (0.36 g) was added under ice-cooling conditions, followed by stirring for 30 minutes. Diethyl 4-aminobenzylphosphonate (0.54 g) and triethylamine (0.22 g) were then added in this order, followed by stirring under ice-cooling conditions for 2 hours, after which the reaction mixture was poured into water and extracted with ethyl acetate. The ethyl acetate layer was washed with water and brine, and dried (MgSO₄), after which the solvent was evaporated off. The residue was subjected to silica gel column chromatography and eluted with ethyl acetate-hexane (1:2, v/v) to yield 7-cyclohexyl-N-(4-diethoxyphosphorylmethylphenyl)-3,4-dihydronaphthalene-2-carboxamide (0.43 g, 45%) as colorless prisms having a melting point of 137°–138° C.

EXAMPLE 2

Iodotrimethylsilane [(CH₃)₃SiI] (0.458 g) was added to a suspension of 7-cyclohexyl-N-(4-diethoxyphosphorylmethylphenyl)-3,4-dihydronaphthalene-2-carboxamide (0.5 g) in carbon tetrachloride (10 ml) at 0° C. After stirring at 0° C. for 1 hour and then at room temperature for 15 hours, this mixture was concentrated under reduced pressure. To the residue, methanol (6 ml) was added; this mixture was acidified with 1N HCl and stirred at room temperature for 30 minutes. The resulting crystals were collected by filtration and recrystallized from methanol-water to yield 7-cyclohexyl-N-(4-phosphonomethylphenyl)-3,4-dihydronaphthalene-2-carboxamide (0.28 g, 63%) as pale yellow prisms having a melting point of 203°–205° C.

EXAMPLE 3

Oxalyl chloride (0.305 g) was added to a solution of 7-cyclohexyl-3,4-dihydronaphthalene-2-carboxamide (0.5 g) in tetrahydrofuran (20 ml), followed by addition of N,N-dimethylformamide (1 drop). After stirring at room temperature for 1 hour, this reaction mixture was concentrated under reduced pressure. The residue was dissolved in tetrahydrofuran (20 ml); this solution was added dropwise to a mixture of diethyl 3-aminobenzylphosphonate (0.54 g), triethylamine (0.223 g) and tetrahydrofuran (20 ml). After 5 stirring at room temperature for 2 hours, the reaction mixture was poured into water and extracted with chloroform. The chloroform layer was washed with water and brine, and dried (MgSO₄), after which the solvent was distilled off. The residue was subjected to silica gel column chromatography and eluted with chloroform-methanol (20:1, v/v) to yield 7-cyclohexyl-N-(3-diethoxyphosphorylmethylphenyl)-3,4-dihydronaphthalene-2-carboxamide (0.23 g, 24%) as colorless crystals having a melting point of 54°–56° C.

EXAMPLE 4

7-Cyclohexyl-3,4-dihydronaphthalene-2-carboxamide and diethyl 2-aminobenzylphosphonate were reacted in the same manner as in Example 3 to yield 7-cyclohexyl-N-(2-diethoxyphosphorylmethylphenyl)-3,4-dihydronaphthalene-2-carboxamide (53%), which was then recrystallized from ethanol-water to yield colorless crystals having a melting point of 102°–103° C.

EXAMPLES 5 THROUGH 18

The compounds listed in Table 2 were prepared in the same manner as in Example 3.

TABLE 2

[Structure: naphthalene with A² at 5/6, A¹ at 7/8 positions, dihydronaphthalene-CONH-phenyl-CH₂P(O)(OR)₂]

| Example Number | $A^1, A^2$ | R | Yield (%) | Melting Point (°C.) | Recrystallization Solvent |
|---|---|---|---|---|---|
| 5 | H, H | $CH_3$ | 66 | 149–151 | ethyl acetate-hexane |
| 6 | H, H | $C_2H_5$ | 66 | 140–141 | ethyl acetate-hexane |
| 7 | H, H | $(CH_3)_2CH$ | 40 | 131–132 | chloroform-hexane |
| 8 | 6-$CH_3O$, H | $CH_3$ | 52 | 186–187 | chloroform-hexane |
| 9 | 6-$CH_3O$, H | $C_2H_5$ | 71 | 157–158 | ethyl acetate-hexane |
| 10 | 7-cyclohexyl, H | $CH_3$ | 63 | 179–181 | ethyl acetate |
| 11 | 7-cyclohexyl, H | $(CH_3)_2CH$ | 42 | 130–131 | ethyl acetate-hexane |
| 12 | 7-$(CH_3)_2CH$, H | $CH_3$ | 43 | 130–132 | ethyl acetate-hexane |
| 13 | 7-$(CH_3)_2CH$, H | $C_2H_5$ | 50 | 97–98 | ethyl acetate-hexane |
| 14 | 6,7-$(C_3H_7O)_2$ | $CH_3$ | 28 | 132–133 | ethyl acetate-isopropyl ether |
| 15 | 6,7-$(CH_3)_2$ | $CH_3$ | 63 | 193–195 | chloroform-hexane |
| 16 | 6,7-$(CH_3)_2$ | $C_2H_5$ | 50 | 196–198 | chloroform-hexane |
| 17 | 5,7-$(CH_3)_2$ | $CH_3$ | 57 | 155–157 | ethyl acetate-hexane |
| 18 | 5,7-$(CH_3)_2$ | $C_2H_5$ | 67 | 162–164 | ethyl acetate-hexane |

EXAMPLES 19 THROUGH 30

The compounds listed in Table 3 were prepared in the same manner as in Example 3.

TABLE 3

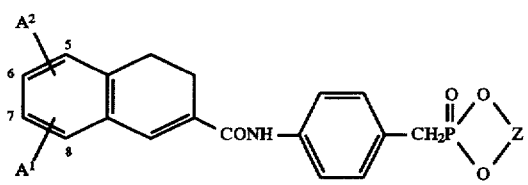

| Example Number | $A^1, A^2$ | Z | Yield (%) | Melting Point (°C.) | Recrystallization Solvent |
|---|---|---|---|---|---|
| 19 | 7-cyclohexyl, H | $-(CH_2)_3-$ | 25 | 237–238 | dichloromethane-hexane |

TABLE 3-continued

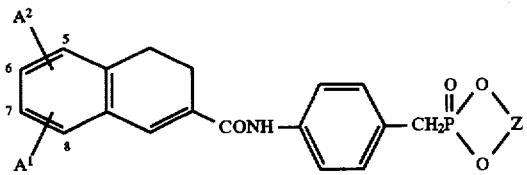

| Example Number | $A^1, A^2$ | Z | Yield (%) | Melting Point (°C.) | Recrystallization Solvent |
|---|---|---|---|---|---|
| 20 | 7-cyclohexyl, H | —CH$_2$—C(C$_4$H$_9$)(C$_2$H$_5$)—CH$_2$— | 55 | 154–156 | ethyl acetate-hexane |
| 21 | 7-cyclohexyl, H | —CH$_2$—C(CH$_3$)(CH$_3$)—CH$_2$— | 62 | 243–244 | chloroform-hexane |
| 22 | 7-cyclohexyl, H | —CH$_2$—C(CH$_3$)(C$_2$H$_5$)—CH$_2$— | 62 | 234–236 | chloroform-hexane |
| 23 | 7-cyclohexyl, H | —CH(CH$_3$)—CH$_2$—CH(CH$_3$)— | 41 | 175–177 | chloroform-hexane |
| 24 | 7-cyclohexyl, H | —CH$_2$—CH(CH$_3$)—CH$_2$— | 56 | 218–220 | chloroform-hexane |
| 25 | 7-cyclohexyl, H | —(CH$_2$)$_4$— | 66 | 184–186 | ethyl acetate-hexane |
| 26 | 7-cyclohexyl, H | —CH$_2$—C(C$_2$H$_5$)(C$_2$H$_5$)—CH$_2$— | 66 | 217–219 | chloroform-hexane |
| 27 | 6,7-(CH$_3$)$_2$ | —(CH$_2$)$_3$— | 45 | 235–237 | chloroform-hexane |
| 28 | 5,7-(CH$_3$)$_2$ | —(CH$_2$)$_3$— | 31 | 269–271 | chloroform-hexane |
| 29 | 7-(CH$_3$)$_2$CH, H | —(CH$_2$)$_3$— | 47 | 206–207 | chloroform-hexane |
| 30 | 6-CH$_3$O, H | —(CH$_2$)$_3$— | 44 | 222–224 | ethyl acetate-hexane |

EXAMPLES 31 THROUGH 33

The compounds listed in Table 4 were prepared in the same manner as in Example 3.

TABLE 4

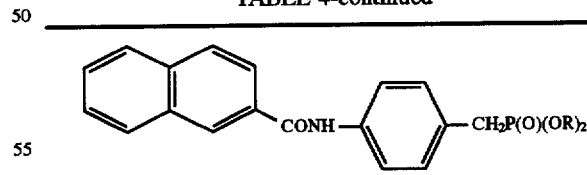

| Example Number | R | Yield (%) | Melting Point (°C.) | Recrystallization Solvent |
|---|---|---|---|---|
| 31 | CH$_3$ | 59 | 154–156 | ethyl acetate-hexane |
| 32 | C$_2$H$_5$ | 72 | 174–175 | ethyl acetate-hexane |
| 33 | (CH$_3$)$_2$CH | 60 | 144–145 | ethyl acetate-hexane |

EXAMPLES 34 THROUGH 37

The compounds listed in Table 5 were prepared in the same manner as in Example 3.

TABLE 5

[Structure: naphthalene-CONH-phenyl-CH₂-P(=O)(O-Z-O) cyclic phosphonate]

| Example Number | Z | Yield (%) | Melting Point (°C.) | Recrystallization Solvent |
|---|---|---|---|---|
| 34* | —(CH₂)₃— | 42 | 250–252 | chloroform-hexane |
| 35 | —CH₂—C(CH₃)(CH₃)—CH₂— | 68 | 218–220 | chloroform-hexane |
| 36 | —CH(CH₃)—CH₂—CH(CH₃)— | 55 | 229–231 | chloroform-hexane |

TABLE 5-continued

[Structure: naphthalene-CONH-phenyl-CH₂-P(=O)(O-Z-O) cyclic phosphonate]

| Example Number | Z | Yield (%) | Melting Point (°C.) | Recrystallization Solvent |
|---|---|---|---|---|
| 37 | —(CH₂)₄— | 65 | 174–176 | chloroform-hexane |

EXAMPLES 38 THROUGH 44

The compounds listed in Table 6 were prepared in the same manner as in Example 3.

TABLE 6

| Example Number | Structure | Yield (%) | Melting Point (°C.) | Recrystallization Solvent |
|---|---|---|---|---|
| 38 | 6,7-dimethoxy-benzocycloheptene-CONH-C₆H₄-CH₂P(O)(OCH₃)₂ | 66 | 153–155 | ethyl acetate-hexane |
| 39 | 6,7-dimethoxy-benzocycloheptene-CONH-C₆H₄-CH₂P(O)(OC₂H₅)₂ | 68 | 139–141 | ethyl acetate-hexane |
| 40 | 6,7-dimethoxy-benzocycloheptene-CONH-C₆H₄-CH₂P(O)[OCH(CH₃)₂]₂ | 48 | 135–136 | chloroform-ethyl acetate-hexane |
| 41 | 6,7-dimethoxy-benzothiepine-CONH-C₆H₄-CH₂P(O)(OCH₃)₂ | 57 | 158–159 | ethyl acetate-isopropyl ether |

TABLE 6-continued

| Example Number | Yield (%) | Melting Point (°C.) | Recrystallization Solvent |
|---|---|---|---|
| 42 | 29 | 175–177 | chloroform-hexane |
| 43 | 55 | 200–201 | ethyl acetate-hexane |
| 44 | 21 | 237–238 | ethyl acetate-hexane |

EXAMPLES 45 AND 46

The compounds listed in Table 7 were prepared in the same manner as in Example 1.

TABLE 7

| Example Number | Yield (%) | Melting Point (°C.) | Recrystallization Solvent |
|---|---|---|---|
| 45 | 50 | 245–246 | dichloromethane-chloroform |
| 46 | 15 | 283–284 | chloroform |

EXAMPLES 47–76

The compound listed in Tables 8, 9 and 10 were prepared in the same as in Example 3.

TABLE 8

| Example Number | Yield (%) | Melting Point (°C.) | Recrystallization Solvent |
|---|---|---|---|
| 47 | 49 | 179–181 | ethyl acetate-hexane |

TABLE 8-continued

| Example Number | Yield (%) | Melting Point (°C.) | Recrystallization Solvent |
|---|---|---|---|
| 48 [naphthalene-CONH-C6H4-CH2P(O)[OCH(CH3)2]2] | 67 | 162–164 | ethyl acetate-hexane |
| 49 [naphthalene-CONH-C6H4-CH2P(O)(OCH3)2] | 67 | 188–189 | chloroform-hexane |
| 50 [naphthalene-CONH-C6H4-CH2P(O) with cyclic (CH2)3 dioxaphosphorinane] | 54 | 235–237 | dichloromethane-hexane |
| 51 [naphthalene-CONH-C6H4-CH2P(O) with cyclic neopentyl dioxaphosphorinane, C(CH3)2] | 29 | >300 | dichloromethane-methanol |
| 52 [naphthalene-CONH-C6H4-CH2P(O) with cyclic bis-methyl dioxaphosphorinane] | 71 | 211–213 | chloroform-hexane |
| 53 [naphthalene-CONH-C6H4-CH2P(O) with cyclic (CH2)4 dioxaphosphepane] | 68 | 225–227 | chloroform-hexane |
| 54 [6-cyclohexyl-tetrahydronaphthalene-CONH-naphthyl-CH2P(O)(OCH3)2] | 35 | 88–89 | ethyl acetate-hexane |

TABLE 8-continued

| Example Number | Structure | Yield (%) | Melting Point (°C.) | Recrystallization Solvent |
|---|---|---|---|---|
| 55 | cyclohexyl-tetrahydronaphthalene-CONH-naphthalene-CH₂P(O)(OC₂H₅)₂ | 47 | 163–164 | ethyl acetate-hexane |
| 56 | cyclohexyl-tetrahydronaphthalene-CONH-C₆H₄-CH(OH)P(O)(OC₂H₅)₂ | 34 | 158–159 | ethyl acetate-hexane |

TABLE 9

| Example Number | Structure | Yield (%) | Melting Point (°C.) | Recrystallization Solvent |
|---|---|---|---|---|
| 57 | cyclohexyl-tetrahydronaphthalene-CONH-(thiophene)-CH₂P(O)(OC₂H₅)₂ | 71 | 160–162 | ethyl acetate-hexane |
| 58 | quinoline-CONH-C₆H₄-CH₂P(O)(OCH₃)₂ | 60 | 195–197 | chloroform-hexane |
| 59 | quinoline-CONH-C₆H₄-CH₂P(O)(OC₂H₅)₂ | 51 | 181–183 | chloroform-hexane |
| 60 | quinoline-CONH-C₆H₄-CH₂P(cyclic phosphonate) | 40 | 232–233 | ethanol |
| 61 | cyclohexyl-tetrahydronaphthalene-CONH-(thiophene)-CH₂P(O)(OCH₃)₂ | 42 | 168–169 | chloroform-hexane |
| 62 | benzofuran-CONH-C₆H₄-CH₂P(O)(OCH₃)₂ | 69 | 171–172 | chloroform-hexane |
| 63 | benzofuran-CONH-C₆H₄-CH₂P(O)(OC₂H₅)₂ | 71 | 152–154 | ethyl acetate-hexane |

TABLE 9-continued

| Example Number | Structure | Yield (%) | Melting Point (°C.) | Recrystallization Solvent |
|---|---|---|---|---|
| 64 | benzofuran-2-CONH—C6H4—CH2P(O)(OCH2CH2CH2O) (cyclic) | 31 | 243–245 | ethanol |
| 65 | (CH3)3C-6-(3,4-dihydronaphthalen-2-yl)-CONH—C6H4—CH2P(O)(OC2H5)2 | 63 | 102–104 | ethyl acetate-hexane |
| 66 | (CH3)3C-6-(3,4-dihydronaphthalen-2-yl)-CONH—C6H4—CH2P(O)(OCH3)2 | 66 | 191–193 | ethyl acetate-hexane |

TABLE 10

| Example Number | Structure | Yield (%) | Melting Point (°C.) | Recrystallization Solvent |
|---|---|---|---|---|
| 67 | (CH3)3C-6-(3,4-dihydronaphthalen-2-yl)-CONH—C6H4—CH2P(O)(OCH2CH2CH2O) (cyclic) | 39 | 224–226 | ethyl acetate-hexane |
| 68 | (CH3)3C-6-(3,4-dihydronaphthalen-2-yl)-CONH—C6H4—CH2P(O)(O-(CH2)4-O) (cyclic) | 42 | 223–225 | ethyl acetate-hexane |
| 69 | phenyl-6-(3,4-dihydronaphthalen-2-yl)-CONH—C6H4—CH2P(O)(OCH3)2 | 56 | 158–159 | ethyl acetate-hexane |
| 70 | phenyl-6-(3,4-dihydronaphthalen-2-yl)-CONH—C6H4—CH2P(O)(OC2H5)2 | 60 | 158–159 | ethyl acetate-hexane |
| 71 | phenyl-6-(3,4-dihydronaphthalen-2-yl)-CONH—C6H4—CH2P(O)(OCH2CH2CH2O) (cyclic) | 61 | 240–242 | methanol |
| 72 | phenyl-6-(3,4-dihydronaphthalen-2-yl)-CONH—C6H4—CH2P(O)(O-(CH2)4-O) (cyclic) | 51 | 224–226 | methanol |

TABLE 10-continued

| Example Number | | Yield (%) | Melting Point (°C.) | Recrystallization Solvent |
|---|---|---|---|---|
| 73 | (structure) | 69 | 166–167 | ethyl acetate-hexane |
| 74 | (structure) | 71 | 154–155 | ethyl acetate-hexane |
| 75 | (structure) | 49 | 238–239 | ethanol |
| 76 | (structure) | 39 | 235–236 | ethanol |

Preparation Examples

An osteogenesis promotor (e.g., prophylactic/therapeutic agent for osteoporosis, bone fracture healing promoter) containing the compound (or salt thereof) of the present invention, represented by formula (I), as an active ingredient can, for example, be produced with the following formulations:

1. Capsules (1) Compound obtained in Example 1 10 mg
(2) Lactose 90 mg
(3) Micronized cellulose 70 mg
(4) Magnesium stearate 10 mg
Total 180 mg per capsule Components (1), (2) and (3) and a half portion of component (4) are mixed and granulated. To these granules, the remaining portion of component (4) is added, and the whole mixture is packed in a gelatin capsule.

2. Tablets (1) Compound obtained in Example 32 10 mg
(2) Lactose 35 mg
(3) Corn starch 150 mg
(4) Micronized cellulose 30 mg
(5) Magnesium stearate 5 mg
Total 230 mg per tablet Components (1), (2) and (3), a two-third portion of component (4) and a half portion of component (5) are mixed and granulated. To these granules, the remaining portions of components (4) and (5) are added, and the whole mixture is tableted by compressive tableting.

INDUSTRIAL APPLICABILITY

The compound (I) can be used advantageously to prevent and treat various metabolic bone diseases, such as osteoporosis, in humans and non-human animals because it potently promotes osteogenesis.

What is claimed is:

1. A compound of the formula (I):

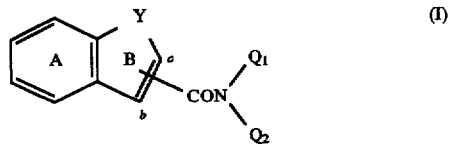

wherein ring A is a benzene ring that may be substituted; Y is a divalent group as a constituent member of ring B forming a 5- to 8-membered ring, said divalent group being (1) —$(CH_2)_{a1}$—O—$(CH_2)_{a2}$— wherein $a_1$ and $a_2$, whether identical or not, represent 0, 1, 2 or 3, the sum of $a_1$ and $a_2$ being not more than 3; —$(CH_2)_{a3}$—O—$(CH_2)_{a4}$—(CH=CH)—$(CH_2)_{a5}$— or —$(CH_2)_{a5}$—(CH=CH)—$(CH_2)_{a4}$—O—$(CH_2)_{a3}$— wherein $a_3$, $a_4$ and $a_5$, whether identical or not, represent 0 or 1, the sum of $a_3$, $a_4$ and $a_5$ being not more than 1, —O—(CH=C=CH)— or —(CH=C=CH)—O—, (2) —$(CH_2)_{b1}$—S—$(CH_2)_{b2}$— wherein $b_1$ and $b_2$, whether identical or not, represent 0, 1, 2 or 3, the sum of $b_1$ and $b_2$ being not more than 3; wherein —$(CH_2)_{b3}$—S—$(CH_2)_{b4}$—(CH=CH)—$(CH_2)_{b5}$— or —$(CH_2)_{b5}$—(CH=CH)—$(CH_2)_{b4}$—S—$(CH_2)_{b3}$— wherein $b_3$, $b_4$ and $b_5$, whether identical or not, represent 0 or 1, the sum of $b_3$, $b_4$ and $b_5$ being not more than 1; —S—(CH=C=CH)— or —(CH=C=CH)—S—, (3) —$(CH_2)_{d1}$— wherein $d_1$ represents 1, 2, 3 or 4; —$(CH_2)_{d2}$—(CH=CH)—$(CH_2)_{d3}$— wherein $d_2$ and $d_3$, whether identical or not, represent 0, 1 or 2, the sum of $d_2$ and $d_3$ being not more than 2; —CH=C=CH—, or (4) —$(CH_2)_{e1}$—NH—$(CH_2)_{e2}$— wherein $e_1$ and $e_2$, whether identical or not, represent 0, 1, 2 or 3, the sum of $e_1$ and $e_2$ being not more than 3; —$(CH_2)_{e3}$—NH—$(CH_2)_{e4}$—(CH=CH)—$(CH_2)_{e5}$— or —$(CH_2)_{e5}$—

(CH=CH)—(CH$_2$)$_{e4}$—NH—(CH$_2$)$_{e3}$— wherein e$_3$, e$_4$ and e$_5$, whether identical or not, represent 0 or 1, the sum of e$_3$, e$_4$ and e$_5$ being not more than 1; —NH—(CH=C=CH)— or —(CH=C=CH)—NH—, —(CH$_2$)$_{e6}$—(N=CH)—(CH$_2$)$_{e7}$— or (CH$_2$)$_{e7}$—(CH=N)—(CH$_2$)$_{e6}$— wherein e$_6$ and e$_7$, identical or not, represent 0, 1 or 2, the sum of e$_6$ and e$_7$, being not more than 2; —(CH$_2$)$_{e8}$—(N=N)—(CH$_2$)$_{e9}$— wherein e$_8$ and e$_9$ whether identical or not, represent 0, 1 or 2, the sum of e$_8$ and e$_9$ being not more than 2; wherein each of said groups (1), (2), (3) and (4) may be substituted by lower alkyl, oxo or hydroxyl;

Q$_1$: is a group of the formula:

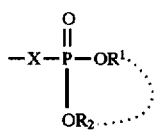 (i)

wherein X is a bond or —E—W—, wherein

E is (1) a divalent alicyclic hydrocarbon group, (2) a divalent alicyclic-aliphatic hydrocarbon group, (3) a divalent aromatic-aliphatic hydrocarbon group, (4) a divalent aromatic hydrocarbon group or (5) a divalent aromatic heterocyclic group, wherein each of said groups may have 1 to 2 substituents, in addition to the group represented by —W—P(O)(OR$^1$)(OR$^2$), W represents a bond or a carbon chain of a chain length of 1 to 4 atoms, which may be substituted;

R$^1$ and R$^2$ are independently hydrogen, or a lower alkyl group, or

R$^1$ and R$^2$ may be combined together to form a ring;

Q$_2$ is hydrogen, a hydrocarbon group that may be substituted or a heterocyclic group that may be substituted; and the group of the formula —CON(Q$_1$)(Q$_2$) is connected to the a- or b-position carbon atom, or a salt thereof.

2. A compound of claim 1, wherein X is (1) a divalent alicyclic hydrocarbon group, (2) a divalent alicyclic-aliphatic hydrocarbon group, (3) a divalent aromatic-aliphatic hydrocarbon group, or (4) a divalent aromatic hydrocarbon group, and ring B is a 5- to 7-membered ring.

3. A compound of claim 1, wherein Q$_1$ is group of the formula:

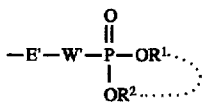

wherein E' is a divalent aromatic hydrocarbon group; W' is a bond or an alkylene group; R$^1$ and R$^2$ are independently hydrogen or a lower alkyl group, or R$^1$ and R$^2$ may be combined together to form a ring.

4. A compound of claim 3, wherein E' is a divalent monocyclic aromatic hydrocarbon group.

5. A compound of claim 4, wherein E' is a phenylene group.

6. A compound of claim 1, wherein R$^1$ and R$^2$ are both a chain lower alkyl group.

7. A compound of claim 6, wherein the lower alkyl has 1 to 6 carbon atoms.

8. A compound of claim 1, wherein R$^1$ and R$^2$ are both ethyl.

9. A compound of claim 1, wherein R$^1$ and R$^2$ are both methyl.

10. A compound of claim 1, wherein R$^1$ and R$^2$ are combined together to form —Z— wherein Z represents a carbon chain of a chain length of 2 to 4 atoms that may have a side chain.

11. A compound of claim 10, wherein Z is —(CH$_2$)$_3$—.

12. A compound of claim 1, wherein Q$_2$ is hydrogen or a lower alkyl.

13. A compound of claim 1, wherein Y is an alkylene chain.

14. A compound of claim 13, wherein the alkylene chain is —(C$_2$)$_2$—.

15. A compound of claim 1, wherein the group of the formula —CON(Q$_1$)(Q$_2$) is connected to the a-position carbon atom.

16. A compound of claim 1, wherein ring A is substituted by an alkyl group or an aromatic hydrocarbon group.

17. A compound of claim 1, which is one of the formula:

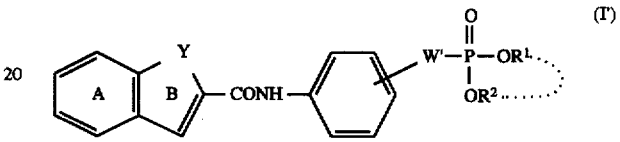 (I')

wherein W' is a bond or an alkylene group; and the other symbols are as defined in claim 1, or a salt thereof.

18. A compound of claim 1, which is 7-cyclohexyl-N-(4-diethoxyphosphorylmethylphenyl)-3,4-dihydronaphthalene-2-carboxamide.

19. A compound of claim 1, which is 7-phenyl-N-(4-diethoxyphosphorylmethylphenyl)-3,4-dihydronaphthalene-2-carboxamide.

20. A compound of claim 1, which is 7-phenyl-N-(4-dimethoxyphosphorylmethylphenyl)-3,4-dihydronaphthalene-2-carboxamide.

21. A method of producing a compound of the formula:

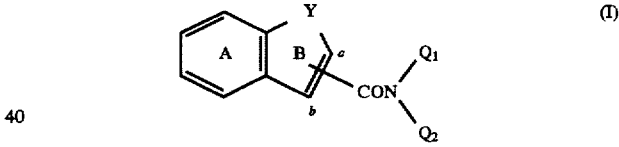 (I)

wherein each symbol is as defined in claim 1, or a salt thereof, by reacting a compound of the formula:

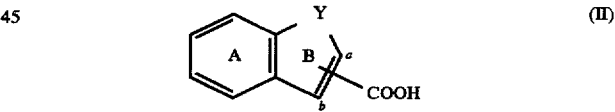 (II)

wherein the —COOH group is connected to the a- or b-position carbon atom and the other symbols are as defined in claim 1, or a reactive derivative thereof, and a compound of the formula:

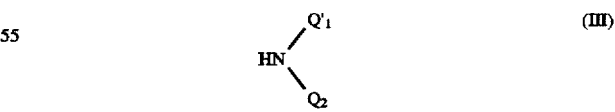 (III)

wherein Q$_1$' is a group of the formula:

 (ii)

wherein R$^3$ and R$^4$ are independently a lower alkyl and the other symbols are as defined in claim 1, optionally followed by phosphonate hydrolysis reaction.

22. A pharmaceutical composition which comprises a therapeutically effective amount of a compound of claim 1 in admixture with a pharmaceutically acceptable carrier, excipient or diluent therefor.

23. A pharmaceutical composition for promoting osteogenesis which comprises a therapeutically effective amount of a compound of claim 1 in admixture with a pharmaceutically acceptable carrier, excipient or diluent therefor.

24. A pharmaceutical composition for promoting bone fracture healing which comprises a therapeutically effective amount of a compound of claim 1 in admixture with a pharmaceutically acceptable carrier, excipient or diluent therefor.

25. A method for treating osteoporosis in a mammal which comprises administering to said mammal a therapeutically effective amount of a compound of claim 1.

* * * * *